(12) United States Patent
Forst et al.

(10) Patent No.: US 12,343,278 B2
(45) Date of Patent: Jul. 1, 2025

(54) HEAD STABILIZATION DEVICE TENSIONING FEATURE AND METHOD OF USE

(71) Applicant: pro med instruments GmbH, Freiburg im Breisgau (DE)

(72) Inventors: Peter Forst, Emmendingen (DE); Matthias Esser, Freiburg (DE); Andreas Blum, Ehrenkirchen (DE); David Devran Culha, Bad Krozingen (DE); Matthias Edgar Schuele, Freiburg (DE)

(73) Assignee: pro med instruments GmbH, Freiburg im Breisgau (DE)

( * ) Notice: Subject to any disclaimer, the term of this patent is extended or adjusted under 35 U.S.C. 154(b) by 483 days.

(21) Appl. No.: 17/162,029

(22) Filed: Jan. 29, 2021

(65) Prior Publication Data

US 2021/0236321 A1 Aug. 5, 2021

Related U.S. Application Data

(60) Provisional application No. 63/091,572, filed on Oct. 14, 2020, provisional application No. 62/967,712, filed on Jan. 30, 2020.

(51) Int. Cl.
*A61F 5/37* (2006.01)

(52) U.S. Cl.
CPC .......... *A61F 5/3707* (2013.01); *A61F 5/3769* (2013.01)

(58) Field of Classification Search
CPC ................ A61B 90/14; A61B 17/6433; A61B 2090/064; A61B 90/10; A61B 17/60;
(Continued)

(56) References Cited

U.S. PATENT DOCUMENTS 9,204,818 B2 * 12/2015 Moffatt ................ A61B 6/4441
9,844,482 B2 * 12/2017 Radina ............... A61G 13/1295
(Continued)

FOREIGN PATENT DOCUMENTS

EP 1152727 A1 11/2001
EP 2614790 A1 7/2013
(Continued)

OTHER PUBLICATIONS

International Search Report and Written Opinion dated Aug. 18, 2021, for International Application No. PCT/IB2021/000048, 26 pages.
(Continued)

*Primary Examiner* — Michelle J Lee
*Assistant Examiner* — Robin Han
(74) *Attorney, Agent, or Firm* — Frost Brown Todd LLP

(57) ABSTRACT

A head stabilization device useable for stabilizing a head of a patient during a medical procedure includes a modular design where stabilization assemblies of various configurations are interchangeable at receiving portions along a frame. The device includes a tensioning feature positioned away from the stabilization assembly but still operable to increase or decrease an amount of force the stabilization assembly applies to the patient's head. The device includes a locking feature for a stabilization assembly having a rotatable member having one or more stabilization features connected thereto. The device includes an adjustment feature to adjust a spacing between frame members with the adjustment feature providing a continuous range of adjustment rather than finite adjustment increments.

15 Claims, 28 Drawing Sheets

(58) Field of Classification Search
CPC ...... A61B 17/64; A61G 13/121; A61G 13/12; A61G 13/1205; A61G 13/1215; A61G 13/126; A61G 13/128–1295; A61F 5/3707; A61F 5/37; A61F 5/3769
USPC .......................................................... 128/869
See application file for complete search history.

(56) References Cited

U.S. PATENT DOCUMENTS

| | | |
|---|---|---|
| 2006/0190010 A1 | 8/2006 | Easton |
| 2009/0306662 A1 | 12/2009 | Dinkler |
| 2014/0276823 A1 | 9/2014 | Schuele |

FOREIGN PATENT DOCUMENTS

| | | |
|---|---|---|
| EP | 2819607 A1 | 1/2015 |
| EP | 3132767 A1 | 2/2017 |

OTHER PUBLICATIONS

Cranial Stabilization & Brain Retractor Systems, available at https://www.pmisurgical.com/fileadmin/Ressources/Flyer/FLYER_DORO-QR3_MPSC_PRINT_ SP printed Nov. 10, 2021, 6 pages.
Mayfield Infinity XR2 at https://www.integralife.com/file/general/1542033855 printed Nov. 10, 2021, 220 pages.

* cited by examiner

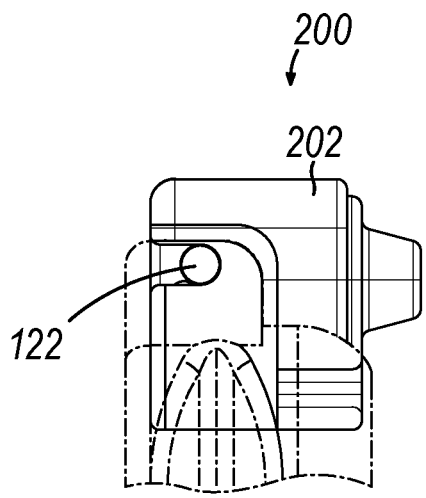 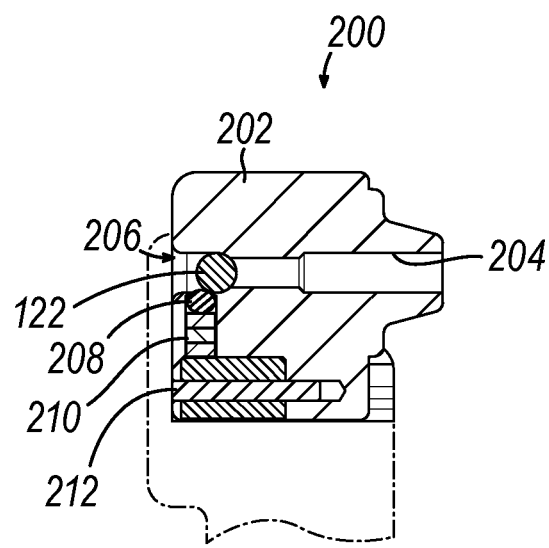
FIG. 4A   FIG. 4B
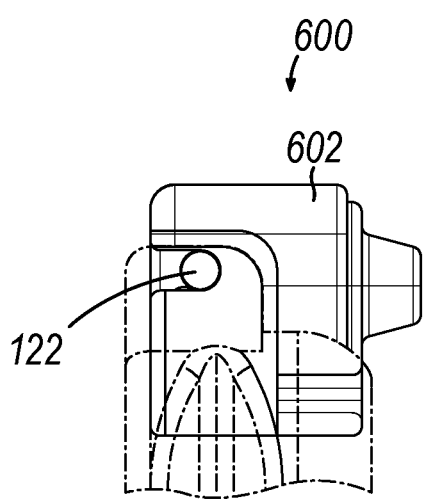 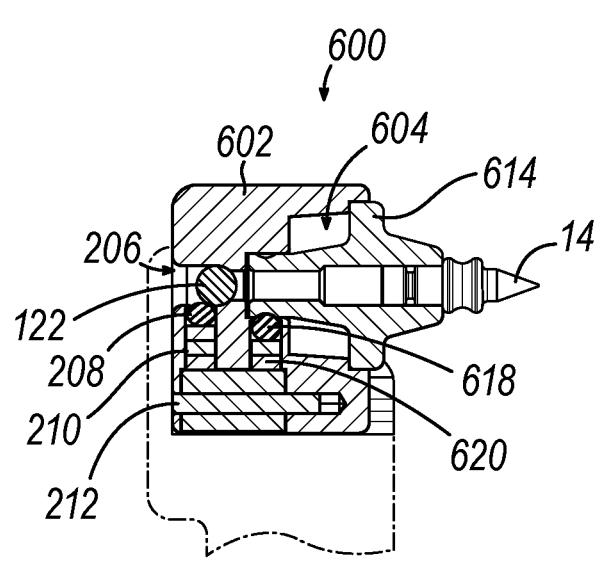
FIG. 5A   FIG. 5B

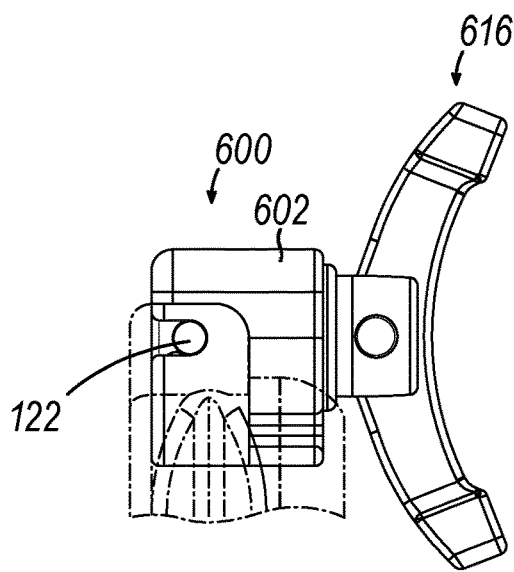
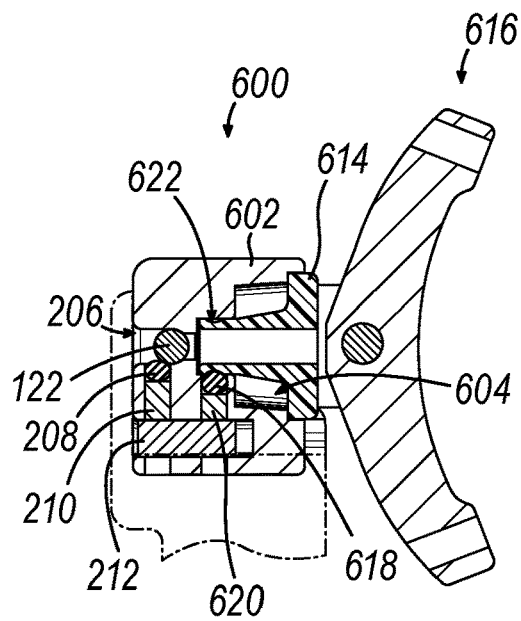
FIG. 6A  FIG. 6B
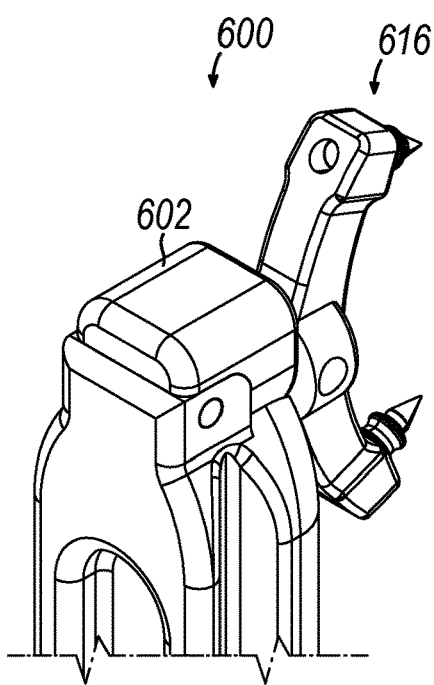
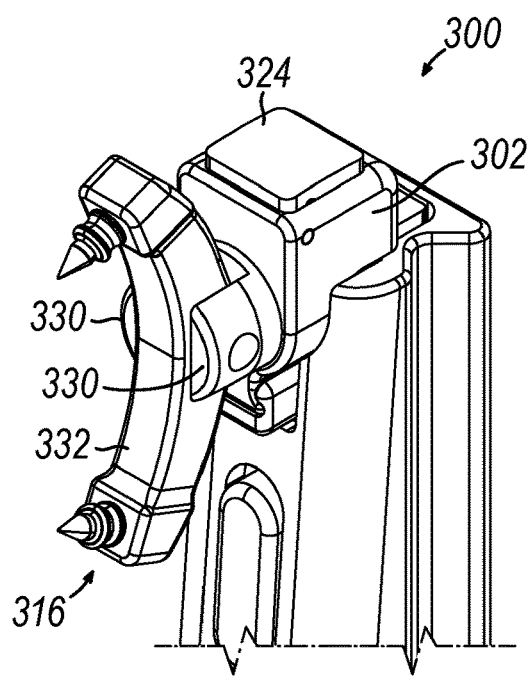
FIG. 6C  FIG. 7A

HEAD STABILIZATION DEVICE TENSIONING FEATURE AND METHOD OF USE

PRIORITY

This application claims priority to U.S. Provisional Patent Application Ser. No. 62/967,712, filed Jan. 30, 2020, entitled "Radiolucent Head Stabilization Device and Method of Use," the disclosure of which is incorporated by reference herein. This application further claims priority to U.S. Provisional Patent Application Ser. No. 63/091,572, filed Oct. 14, 2020, entitled "Head Stabilization Device Tensioning Feature and Method of Use," the disclosure of which is incorporated by reference herein.

BACKGROUND

During certain medical procedures it may be necessary or desirable to stabilize all or a portion of a patient such that the patient or portion of the patient is immobilized. In certain neurological procedures the portion stabilized may include the head and/or neck of the patient. Certain devices and methods may be used to stabilize a certain portion of the patient. For example, a skull clamp is a type of head stabilization device that may be used to stabilize the head and/or neck of the patient. Furthermore, it may also be necessary or desirable to use various imaging modalities to obtain images of the patient before, during, and/or after a procedure.

While a variety of head stabilization devices and method of use of the same have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

FIG. 4A depicts a front elevation view of an exemplary modular pin assembly.

FIG. 4B depicts a cross section view of FIG. 4A.

FIG. 5A depicts a front elevation view of another exemplary modular pin assembly including an adapter.

FIG. 5B depicts a cross section view of FIG. 5A.

FIG. 6A depicts a front elevation view of the exemplary modular pin assembly of FIG. 5A shown with a 2-pin rocker arm assembly.

FIG. 6B depicts a cross section view of FIG. 6A.

FIG. 6C depicts a perspective view of the assembly of FIG. 6A, shown with exemplary skull pins and removable caps for preventing unintended contact with the skull pins.

FIG. 7A depicts a perspective view of an exemplary modular locking 2-pin rocker arm assembly.

Figure 1A:
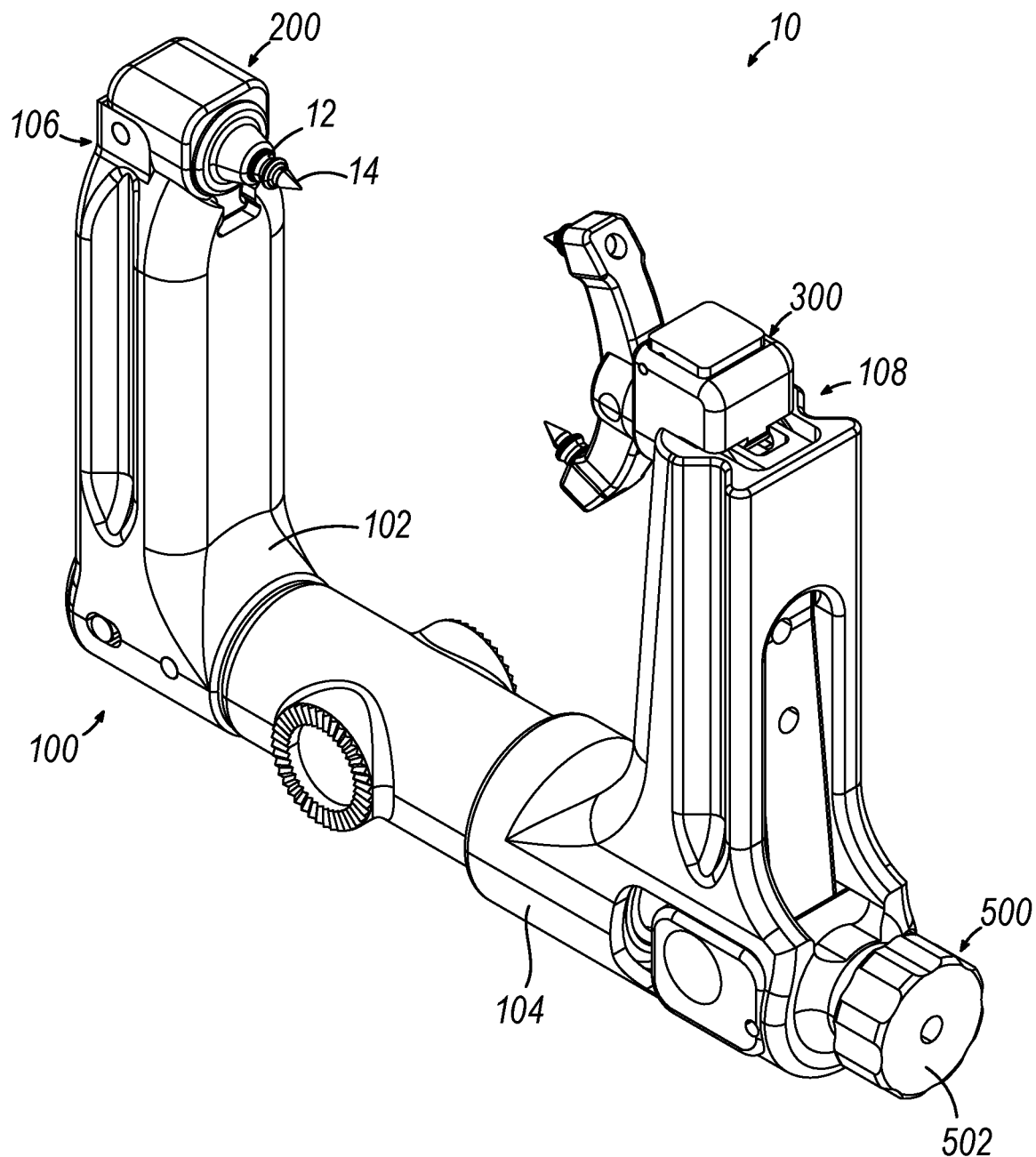
FIG. 1A depicts a perspective view of an exemplary skull clamp.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1B:
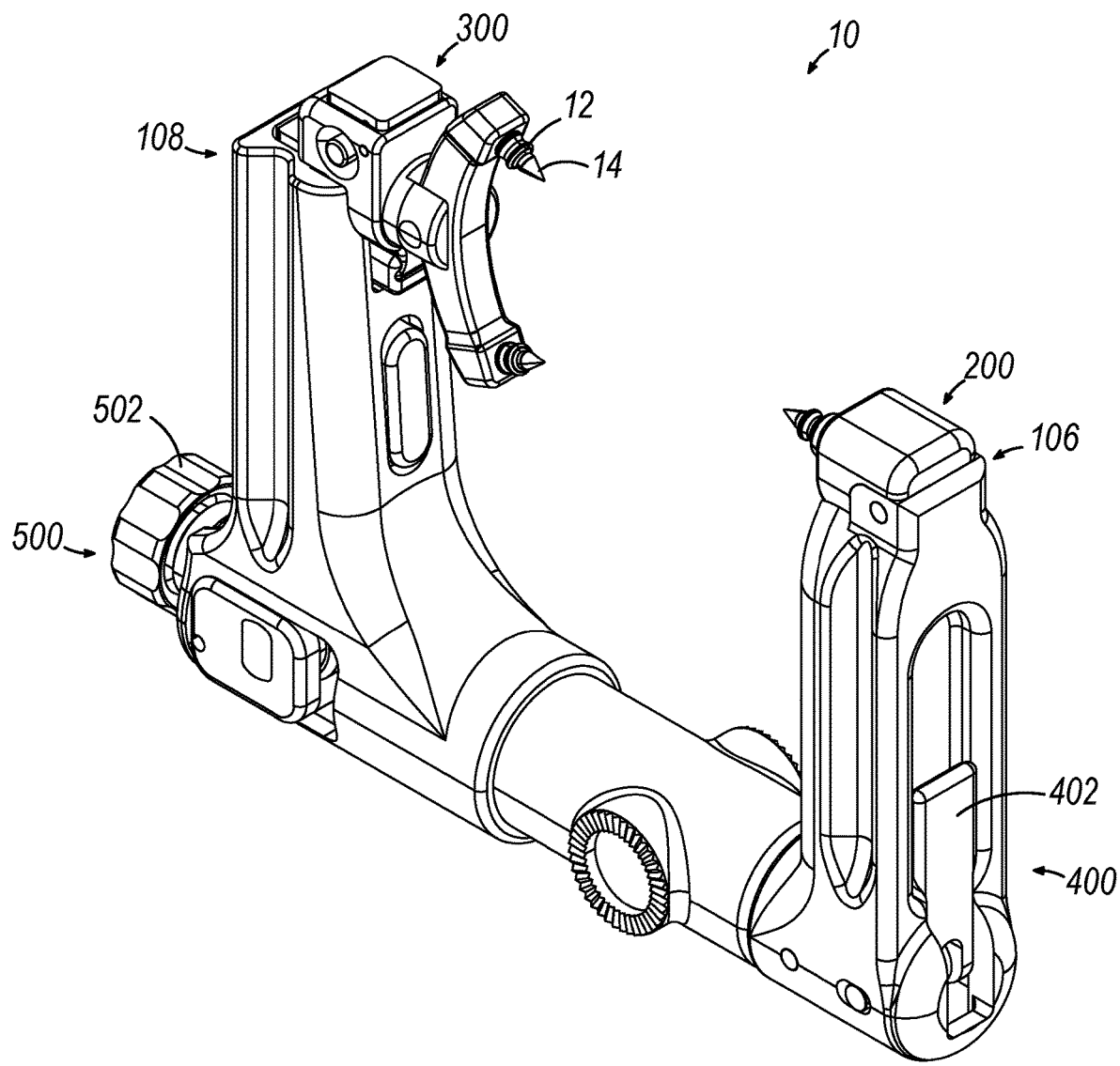
FIG. 1B depicts another perspective view of the skull clamp of FIG. 1A.

FIGS. 1A and 1B illustrate an exemplary head stabilization or fixation device (10). Throughout the specification the term "HFD" is used interchangeably with the terms "head stabilization device," "head fixation device," or "skull clamp." In the illustrated versions here HFD (10) has the shape or form of a skull clamp. In this respect, HFD (10) comprises a frame (100). Frame (100) includes a first frame portion (102) and a second frame portion (104). Frame portions (102, 104) are adjustably connectable to adjust a spacing between them. Frame portions (102, 104) include respective receiving portions (106, 108) that are configured to receive a stabilization assembly. In the illustrated version, stabilization assembly (200) is received by receiving portion (106) of frame portion (102). Furthermore, stabilization assembly (300) is received by receiving portion (108) of frame portion (104).

As seen more clearly in FIG. 1B, HFD (10) includes a frame adjustment feature (400) that is operable to adjust the relative spacing between frame portions (102, 104). Frame adjustment feature (400) includes an actuator (402) as seen in FIG. 1B. Additional components and operability of frame adjustment feature (400) will be discussed in detail below with respect to FIGS. 2A-3.

HFD (10) is configured with a modular design such that receiving portions (106, 108) are configured to receive a variety of stabilization assemblies as opposed to only a single type or design of stabilization assembly. For instance, in the illustrated version of FIGS. 1A and 1B, stabilization assembly (200) and stabilization assembly (300) could be switched with one another such that stabilization assembly (200) connects with receiving portion (108) and similarly stabilization assembly (300) connects with receiving portion (106). Additional components and operability of the modularity of HFD (10) with respect to various stabilization assemblies will be discussed in detail below with respect to FIGS. 4A-7D.

Still referring to FIGS. 1A and 1B, HFD (10) includes a tensioning feature (500) that is operable to adjust an amount of force a stabilization assembly applies to the patient. Tensioning feature (500) includes actuator (502) as seen in FIGS. 1A and 1B. Additional components and operability of tensioning feature (500) will be discussed in detail below with respect to FIGS. 8A-8D.

I. Exemplary Frame Adjustment Feature

Figure 2A:
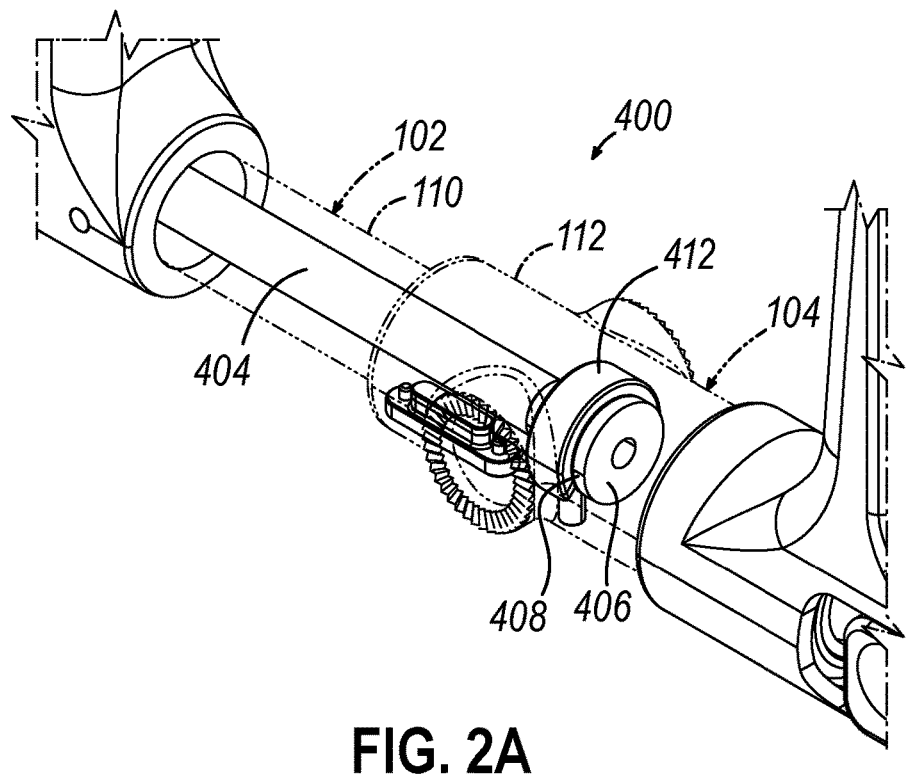
FIG. 2A depicts a partial perspective view of a release feature of the skull clamp of FIG. 1A, with a portion shown in phantom to reveal internal components.
Figure 2B:
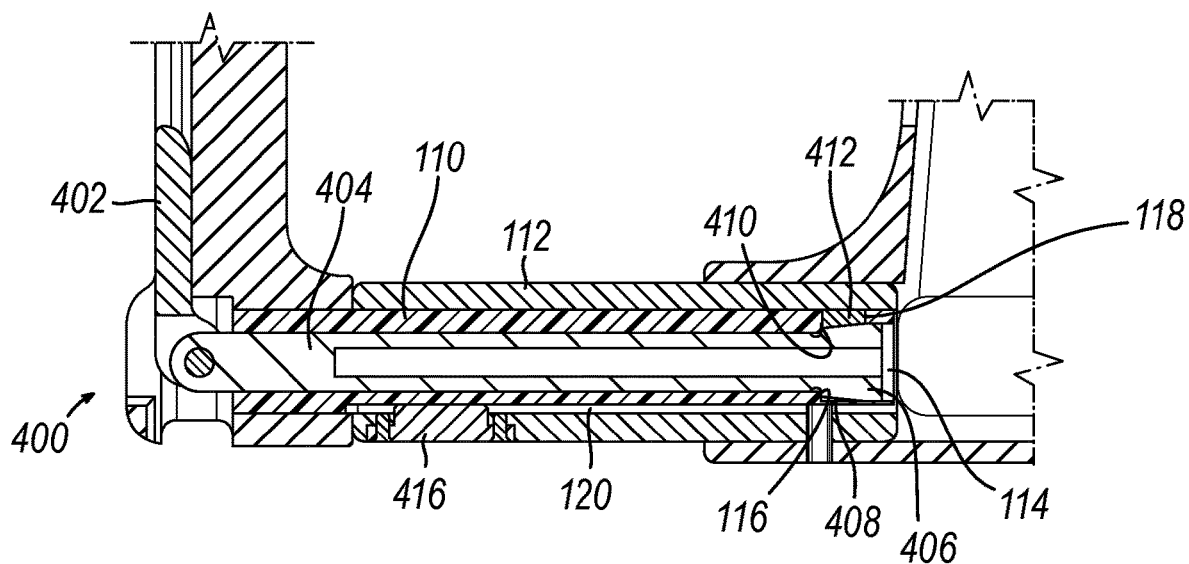
FIG. 2B depicts a partial cross section view of the skull clamp of FIG. 1A, showing the exemplary release feature.
Figure 2C:
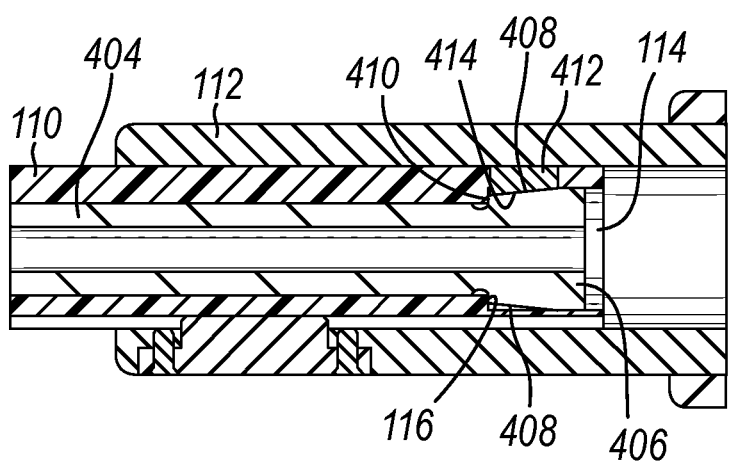
FIG. 2C depicts an enlarged partial cross section view of the skull clamp of FIG. 2B, with the relative position of the arms of the skull clamp in an unloaded condition.

Referring now to FIGS. 2A-2C, frame adjustment feature (400) is shown and will be described in further detail. As shown in FIG. 2A, frame portion (102) includes an elongated shaft (110) that is received within an elongated shaft (112) of frame portion (104). Extending within elongated shaft (110) is a locking feature (404) of frame adjustment feature (400). Locking feature (404) is connectable with actuator (402) via a pinned connection in the present example. As seen in FIGS. 1B and 2B, actuator (402) is rotatable about this pinned connection. When actuator (402) is rotated upwards or vertically as shown in FIG. 2B, actuator (402) pulls or retracts locking feature (404) toward its pinned connection with actuator (402). Conversely, when actuator (402) is rotated in the opposite manner, actuator (402) pushes locking feature (404) away from its pinned connection with actuator (402).

Locking feature (404), in the illustrated version, includes a distal portion (406) that has a sloped or angled outer surface (408). In the present example outer surface (408) is also curved in addition to being sloped or angled. In this manner, in the present example distal portion (406) comprises a tapered or conical shape with the largest diameter at the distal-most end of distal portion (406). Distal portion (406) further comprises a proximal shoulder (410). Elongated shaft (110) includes a hollow interior (114) through which locking feature (404) extends. Hollow interior (114) defines a stop (116) near its distal end that interacts with shoulder (410) to prevent locking feature (404) from being withdrawn from elongated shaft (110) from the actuator side.

Elongated shaft (110) includes an opening (118) near its distal end. Opening (118) is configured to receiving a locking feature (412) that is contactable by distal portion (406) of locking feature (404). Locking feature (412) includes a sloped or angled surface (414) that contacts surface (408) of distal portion (406) of locking feature (404). In this manner, as locking feature (404) is moved toward the side where actuator (402) is located, the interacting sloped surfaces (408, 414) cause locking feature (412) to impinge upon elongated shaft (112) of frame portion (104). This contact is sufficient to create a frictional fit between these components such that frame portions (102, 104) are prevented from moving apart from one another. It should further be noted that in the present example, while frame portions (102, 104) are prevented from moving apart when locking feature (412) is sufficiently engaged with or contacting shaft (112), frame portions (102, 104) may be moved toward one another thus further closing frame (100).

When desiring to open frame (100), the process described above is basically reversed. In particular, actuator (402) is rotated downward away from its perpendicular orientation relative to locking feature (404). This moves locking feature (404) in the direction of frame portion (104), which allows for distal portion (406) to disengage from locking feature (412) such that locking feature (412) thereby disengages with shaft (112) to an extent where any frictional forces can be overcome and frame portions (102, 104) adjusted to a more open arrangement as desired.

In the manner described above, frame adjustment feature (400) is configured such that frame portions (102, 104) may be adjusted relative to each other and then secured to prevent opening of frame portions (102, 104) once a desired position or arrangement has been reached. Moreover, the increments for adjusting the relative position of frame portions (102, 104) is infinitely variable with this locking configuration having a friction fit between components as opposed to a mechanical fit of complementary structures like engaging teeth where the increment of adjustment is limited by the dimensions of the mechanical engaging structures. In other words, in the illustrated example, the configuration of locking feature (412), distal portion (406), and shaft (112) is such that a stepless fit is achieved. In this manner, the range of adjustment of frame portions (102, 104) is infinitely variable in contrast to those devices where interlocking engagement features or stepped features are used to control and regulate adjustment increments of frame portions (102, 104). Of course in some other versions, a stepped or engaging feature or features could be included with locking features (404, 412) if an interference fit or lock were desired. In view of the teachings herein, such modification among others will be apparent to those of ordinary skill in the art.

As best seen in FIGS. 2B and 2C, elongated shaft (110) includes a groove (120) along a bottom region. Alignment feature (416) is configured to extend through elongated shaft (112) and be received within groove (120) to maintain the alignment of elongated shafts (110, 112) such that they are prevented from changing relative rotational position when adjusting the spacing of frame portions (102, 104).

Figure 3:
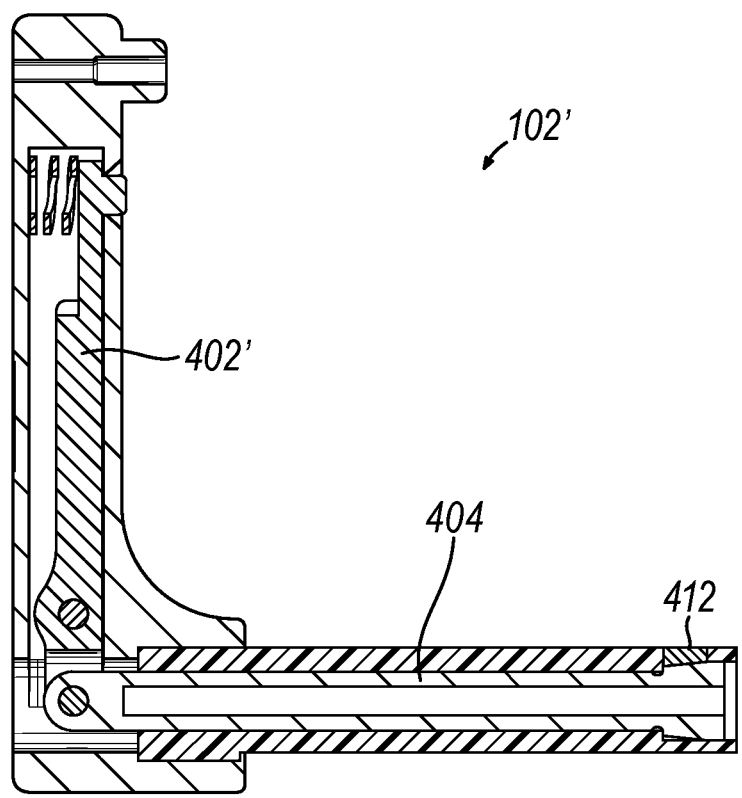
FIG. 3 depicts a cross section view of another exemplary arm usable with the skull clamp of FIG. 1A and having another exemplary release feature.

FIG. 3 illustrates an alternate frame portion (102') usable in place of frame portion (102) with HFD (10). Frame portion (102') is similar to frame portion (102) with the exception of having a different actuator configuration. Frame portion (102') comprises actuator (402') which connects with locking feature (404). Actuator (402') includes a depressible portion proximate or near to the stabilization assembly and along an upright portion of frame portion (102'). In this example, actuator (402') is biased by a spring such that locking feature (404) is biased away from frame portion (104) and thereby distal portion (406) contacts locking feature (412) to cause the frictional lock or friction fit between frame portions (102', 104). Depressing actuator (402') overcomes the spring bias and pushes locking feature (404) toward frame portion (104), which thereby reduces or removes the frictional lock or friction fit and permits for opening or increasing the spacing between frame portions (102', 104).

II. Exemplary Modular Stabilization Assemblies

FIGS. 4A and 4B illustrate stabilization assembly (200). Stabilization assembly (200) comprises a housing (202). Housing (202) includes a bore (204) configured to receive a pin carrier (12) with a pin (14) that is configured to contact the patient. Housing (202) includes a proximal cut-out (206) configured to receive a pin (122) that extends through a receiving portion (106, 108) depending on which frame portion (102, 104) stabilization assembly (200) is being installed upon. Within housing (202) is a spherical member (208) that is in contact with a resilient member (210). A pin (212) or pin (212) and body combination are located beneath resilient member (210).

When installing stabilization assembly (200), housing (202) is slid or translated proximally to fit within the receiving portion (106, 108). Housing (202) and receiving portion (106, 108) include complementary engaging features, for example complementary dovetail features, that guide stabilization assembly (200) into place and keeps housing (202) in specific orientation. Pin (122) aligns with cut-out (206) and contacts spherical member (208), which is then pressed downward against resilient member (210). This allows displacement of spherical member (208) so that pin (122) can be fully seated within cut-out (206). Once fully seated, pin (122) clears spherical member (208), which then returns behind pin (122) based on the bias of resilient member (210). In this manner, a locking effect is achieved, which retains stabilization assembly (200) in place relative to receiving portion (106, 108).

FIGS. 5A-6C illustrate stabilization assembly (600). Stabilization assembly (600) is similar to stabilization assembly (200) except that stabilization assembly (600) includes a housing (602) with a bore (604) that is configured to receive an adapter (614). In one example, as shown in FIG. 5B, adapter (614) is configured to receive pin (14) that is configured to contact the patient. In another example, as shown in FIGS. 6A and 6B, adapter (614) is configured to receive a rocker arm assembly (616).

To retain adapter (614) in place within bore (604), stabilization assembly (600) includes spherical member (618) and resilient member (620). Adapter (614) includes an annular groove (622) that is configured to interlock with spherical member (618) once adapter (614) is fully seated within bore (604). When inserting adapter (614), spherical member (618) is pushed against resilient member (620) and then when fully seated, annular groove (622) aligns above spherical member (618) such that the bias from resilient member (620) restores the position of spherical member (618) which then engages annular groove (622). With this configuration, adapter (614) is secured from translational movement, but may still rotate with spherical member (618) remaining engaged with annular groove (622).

In another version of stabilization assembly (600), multiple adapters (614) can be used with housing (602) where, for instance, adapter (614) is configured for use with a single pin (14), and another adapter is configured for use with rocker arm assembly (616). In this manner, the modular design allows for interchanging the stabilization feature type by interchanging the adapter associated with the particular stabilization feature type. Again, in other versions like the one described above, the same adapter (614) can be configured for use with multiple stabilization feature types such that the modular design allows for interchanging the stabilization feature type by interchanging the stabilization feature itself and keeping the adapter (614) the same.

Figure 7B:
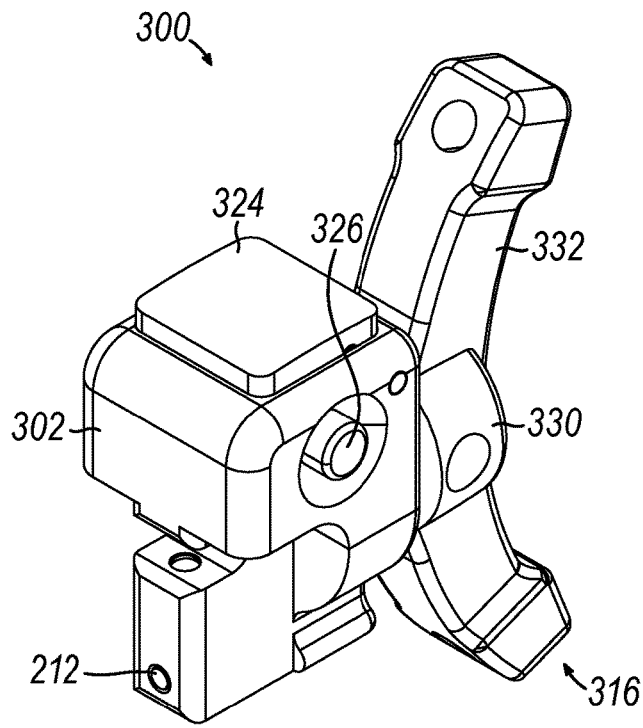
FIG. 7B depicts another perspective view of the assembly of FIG. 7A.

FIGS. 7A-7D depict a stabilization assembly (300) that is configured with a locking rocker arm assembly (316). Stabilization assembly (300) comprises housing (302), actuators (324, 326), spherical members (208, 618), resilient members (210, 620), pin (212), and a bore (304) configured to receive a portion of locking rocker arm assembly (316). Stabilization assembly (300) connects with receiving portions (106, 108) in the same manner as stabilization assembly (200) described above. As seen in FIG. 7A, housing (302) includes dovetail feature in the same manner as stabilization assemblies (200, 600).

Figures 7C, 7D:
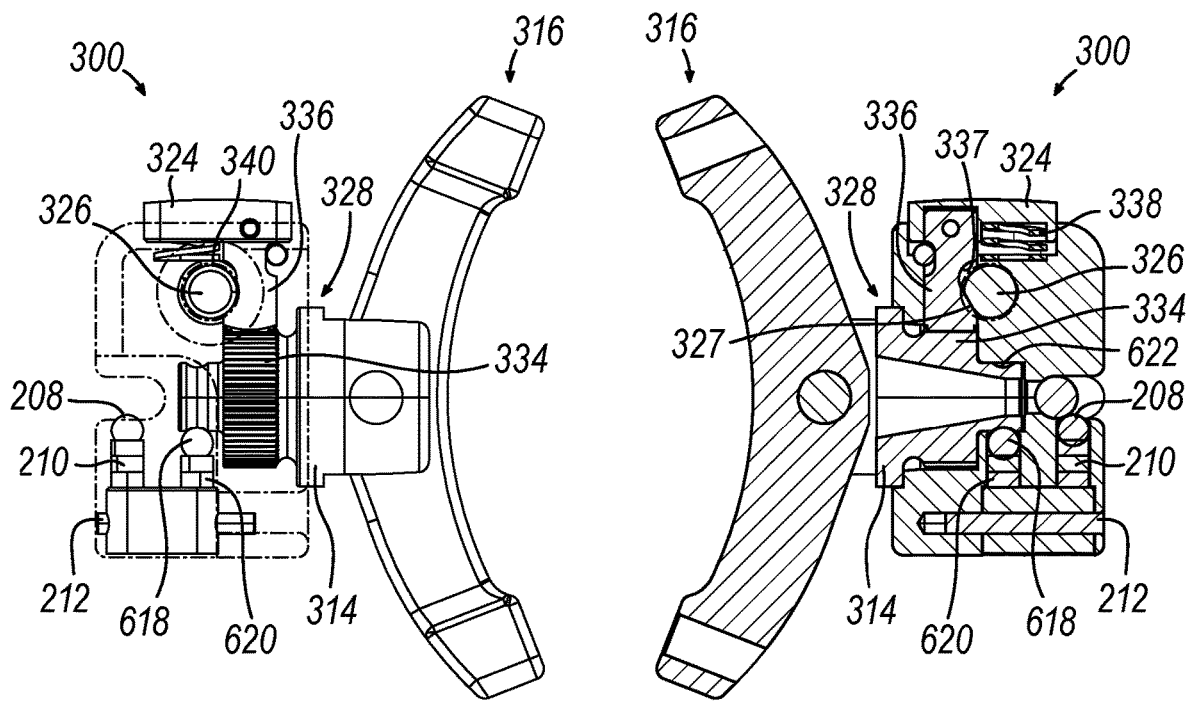
FIG. 7C depicts another perspective view of the assembly of FIG. 7A, showing with a housing in phantom to reveal internal components.
FIG. 7D depicts a cross section view of the assembly of FIG. 7A.

As shown in FIGS. 7C and 7D, locking rocker arm assembly (316) includes a body (328) having a pair of extensions (330) that receive a rocker arm (332) via a pinned connection. Body (328) further includes an adapter (314) similar to adapter (614) but further incorporating locking features that secure a rotational position of locking rocker arm assembly (316). For instance, adapter (314) includes annular flange (622) for engagement with spherical member (618). However, adapter (314) further includes toothed member (334) that is configured to selectively engage with a shaft (336) having a toothed end that is configured to engage with the teeth of toothed member (334). This engagement between shaft (336) and toothed member (334) locks the rotational position of rocker arm (332) relative to housing (302) and frame (100).

When actuators (324, 326) are not depressed, or otherwise in a neutral state with rocker arm (332) locked, a surface (327) of a cut out portion in actuator (326) contacts a surface (337) of a cut out portion in shaft (336) such that shaft (336) maintains locking engagement with toothed member (334). To adjust the rotational position of rocker arm (332), depressing actuator (326) overcomes a bias from spring (340) and causes disengagement of surface (327) with surface (337), further causing the cut-out portion of actuator (326) to align with the cut-out portion of shaft (336) without interference. This alignment without interference allows spring (338) and its natural bias to drive release actuator (324) and connected shaft (336) upwards away from toothed member (334) to disengage the toothed features and thereby permit rotational adjustment. Once the desired rotational adjustment is achieved, release actuator (324) is pressed downward to overcome the bias of spring (338) and align the cut-out portions of shaft (336) and release actuator (326). Furthermore, the bias spring (340) on actuator (326) translates actuator (326) so that surface (327) again contacts surface (337) of shaft (336). In this manner the toothed portion of shaft (336) engages toothed member (334) to lock the rotational position of rocker arm (332).

III. Exemplary Torsion Rod Tensioning Feature

Figure 8A:
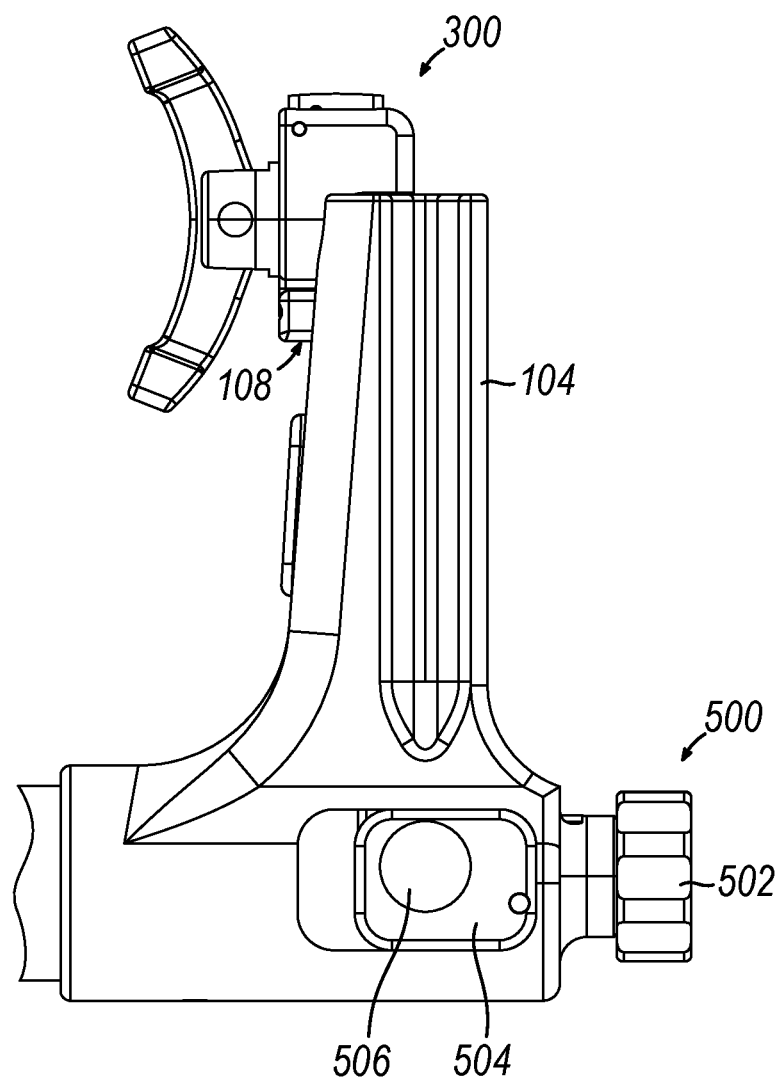
FIG. 8A depicts an arm of the skull clamp of FIG. 1A, showing a pin assembly tension adjustment feature.
Figure 8B:
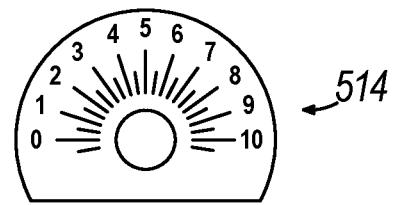
FIG. 8B depicts an exemplary scale that can be incorporated with and used with the arm of FIG. 8A.
Figure 8C:
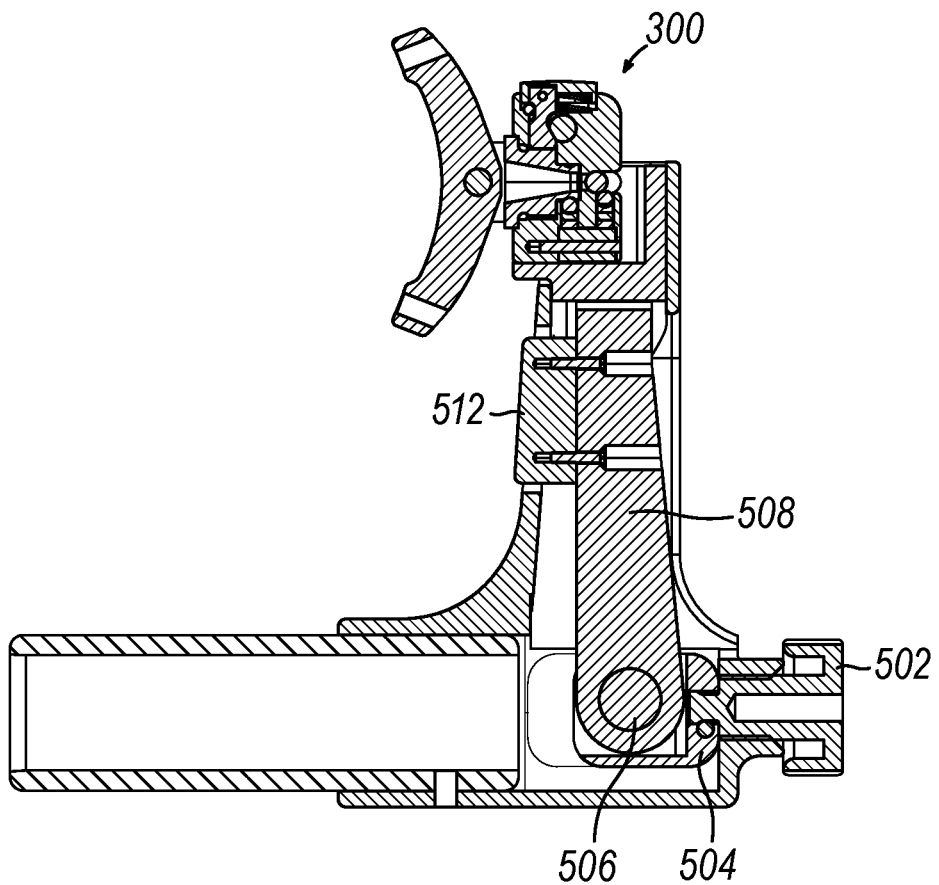
FIG. 8C depicts a cross section view of the arm of FIG. 8A.

FIGS. 8A-8D depict tensioning feature (500) that is used to adjust an amount of force the connected stabilizing assembly imparts on the patient during use of HFD (10). Tensioning feature (500) comprises actuator (502) with an end portion that extends through a bore in frame portion (104) and threadably connects with a body (504). Body (504) comprises a bore that receives a rod (506), which connects an elongated member (508) with body (504). Rod (506) is fastened with body (504) and also includes a polygon shaped profile in at least one location where rod (506) extends through body (504). In this manner, rod (506) is keyed with body (504) and thus rod (506) will not rotate with respect to body (504). Elongated member (508) connects with rod (506) as shown in FIG. 8C. In other locations where rod (506) extends through elongated member (508), rod (506) includes a polygon shaped profile such that elongated member (508) is keyed with rod (506), and thus elongated member (508) will not rotate with respect to rod (506).

Figure 8D:
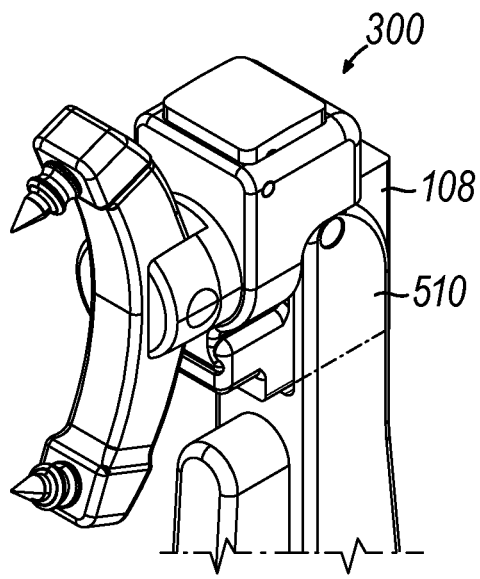
FIG. 8D depicts a perspective view of an upper portion of the arm of FIG. 8A.
Figure 8E:
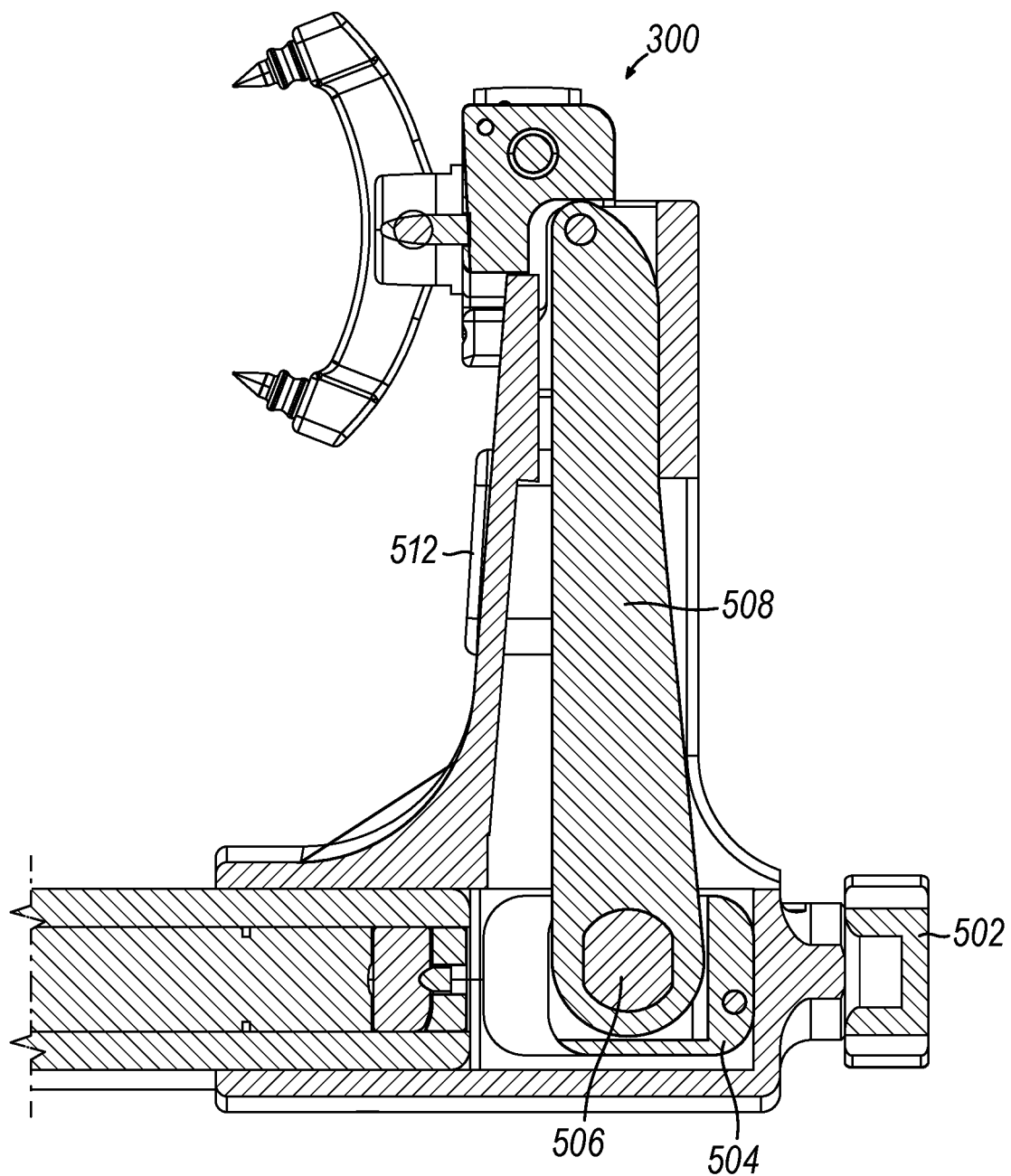
FIG. 8E depicts another cross section view of the arm of FIG. 8A showing a keyed connection between certain components of a tensioning feature.

At another end, elongated member (508) comprises a pair of extensions (510) with a space between them. Within this space, receiving portion (108) is positioned and further makes a pinned connection with the pair of extensions (510). The bore within receiving portion (108) that makes the pinned connection with the pair of extensions (510) is elongated as seen in FIGS. 8C and 8D. This elongated configuration permits some movement of receiving portion (108) laterally.

To adjust tensioning feature (500), actuator (502) is rotated and thereby translates body (504). The direction of translation depends on the direction of rotation of actuator (502). Tension is increased, or in other words the force imparted on the patient is increased, when body (504) is moved toward frame portion (102). This motion causes rod (506) to move in the same direction. With elongated member (508) connected with rod (506), elongated member (508) also moves in the same direction. At its upper end elongated member (508) is pinned with receiving portion (108) as mentioned above. This pinned connection fixes or limits the range of motion elongated member (508) can undergo when HFD (10) is in a loaded state with the patient's head between and contacting the stabilization assemblies and their respective stabilization features. Accordingly, a twisting force or torque on rod (506) exists under these conditions. In this manner, rod (506) acts similar to a torsion rod. Therefore, as body (504) and rod (506) are moved toward frame portion (102), tension within rod (506) and elongated member (508) is increased resulting in elongate member (508) placing a greater force on receiving portion (108). In this manner elongate member (508) acts as a tension member where the tension is adjustable. With a patient's head positioned within HFD (10), receiving portion (108) will remain laterally stationary, and thus the increased tension results in a greater force applied to the patient's head. Reducing the force imparted on the patient's head can be accomplished by rotating actuator (502) in the opposite manner to thereby translate body (504) and rod (506) toward frame portion (104).

Elongated member (508) also includes actuator (512). Actuator (512) is configured as a pre-tensioning feature. In this manner, before pinning the patient within HFD (10), actuator (512) can be depressed to thereby move both frame portions (102, 104) together until the associated stabilizing features contact the patient's head. Once this contact is achieved actuator (512) is released and further tension adjustments may be made using tensioning feature (500) as described above. By way of example only, and not limitation, in some instances, the pre-tensioning feature using actuator (512) can provide a force on the patient's head of about 50 to about 150 newtons.

Referring to FIG. 8B, in some versions a force indication or scale (514) is included with tensioning feature (500). This scale can be configured to correlate the tension within rod (506) and elongated member (508) based on movement of body (504) with a resultant force that is applied to stabilization assembly (300). In one example scale (514) may be included on an outward facing surface of rod (506). In view of the teachings herein, other ways to indicate tension and/or force will be apparent to those of ordinary skill in the art.

IV. Exemplary Alternate Skull Clamp with Bending Beam Tensioning Feature

Figure 9:
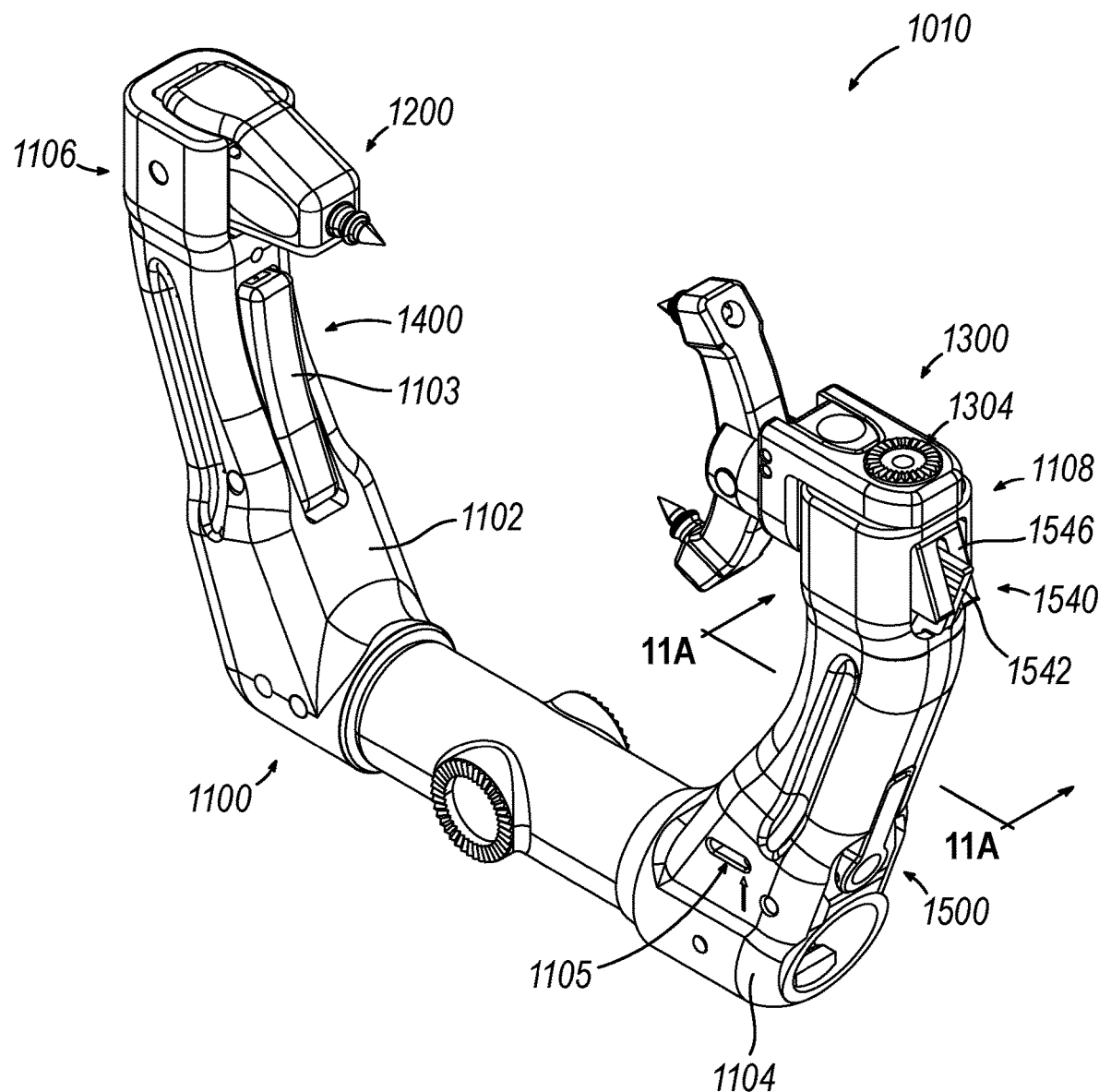
FIG. 9 depicts a perspective view of another exemplary skull clamp.

FIG. 9 illustrates an exemplary alternative HFD (1010) that is substantially similar to HFD (10) described above. For instance, as with HFD (10) described above, HFD (1010) of the present example has the shape or form of a skull clamp. Accordingly, HFD (1010) of the present example comprises a frame (1100) similar to frame (100) described above. Frame (1100) includes a first frame portion (1102) and a second frame portion (1104). Frame portions (1102, 1104) are adjustably connectable to adjust a spacing between them. Frame portions (1102, 1104) include respective receiving portions (1106, 1108) that are configured to receive a stabilization assembly. In the illustrated version, stabilization assembly (1200) is received by receiving portion (1106) of frame portion (1102). Furthermore, stabilization assembly (1300) is received by receiving portion (1108) of frame portion (1104).

As with HFD (10) described above, HFD (1010) of the present example further includes a frame adjustment feature that is operable to adjust the relative spacing between frame portions (1102, 1104). In some versions, the frame adjustment feature may be the same or similar to frame adjustment feature (400) described above. In the present example, HFD (1010) includes frame adjustment feature (1400), which includes a pair of engaging members (not shown) that each have one or more teeth (not shown). In such versions, the teeth of one of the engaging members are configured to selectively engage with the teeth of the other engaging member. An actuation feature (1103), when actuated, is configured to move or displace at least one of the engaging members so that the teeth of each engaging member disengage. When the engaging members are disengaged, the spacing of the frame assembly can be adjusted to a larger or smaller size. When the engaging members are engaged, in some versions the spacing of the frame assembly is fixed, while in other versions the spacing of the frame assembly may still be adjusted to a smaller spacing, but not a larger spacing. With such frame adjustment features, one or more safety features (not shown) may be incorporated such that actuation feature (1103) is prevented from operating unless the one or more safety features are first actuated. In other examples, various alternative frame adjustment features may be readily incorporated into HFD (1010) or HFD (10) as will be appreciated by those of ordinary skill in the art in view of the teachings herein.

As with HFD (10) described above, HFD (1010) of the present example is configured with a modular design such that receiving portions (1106, 1108) are configured to receive a variety of stabilization assemblies as opposed to only a single type or design of stabilization assembly. As similarly described above, stabilization assembly (1200) and stabilization assembly (1300) could be switched with one another such that stabilization assembly (1200) connects with receiving portion (1108) and similarly stabilization assembly (1300) connects with receiving portion (1106). In this manner, the modularity and interchangeability with respect to stabilization assemblies (1200, 1300) and HFD (1010) operates in the same or similar manner as described above with respect to stabilization assemblies (200, 300) and HFD (10).

Figure 10:
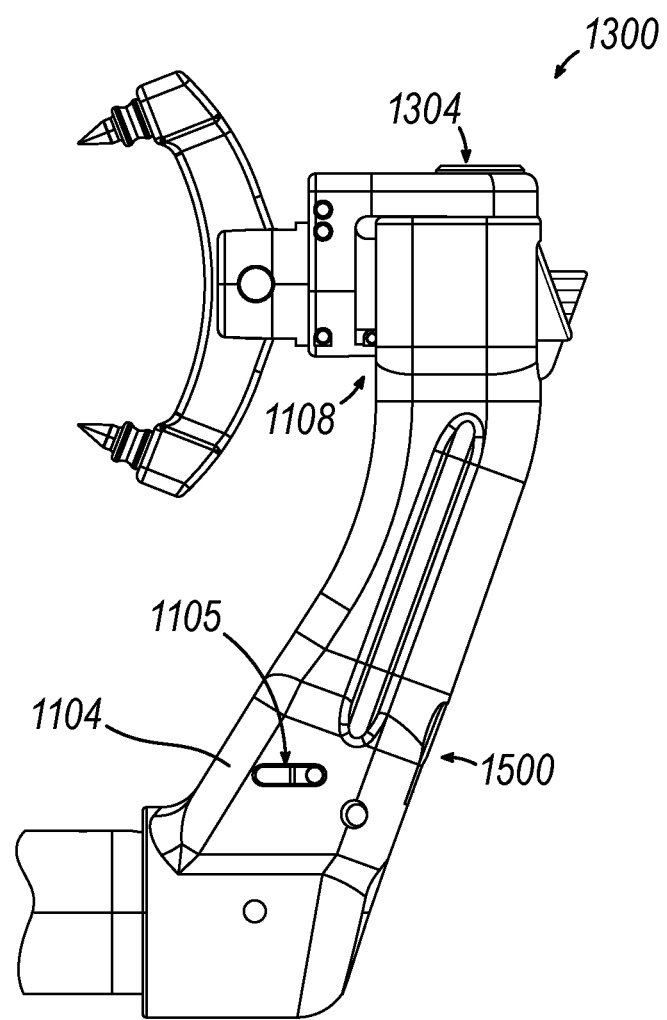
FIG. 10 depicts a side elevational view of an arm of the skull clamp of FIG. 9, showing an alternative tension adjustment feature.
Figure 11A:
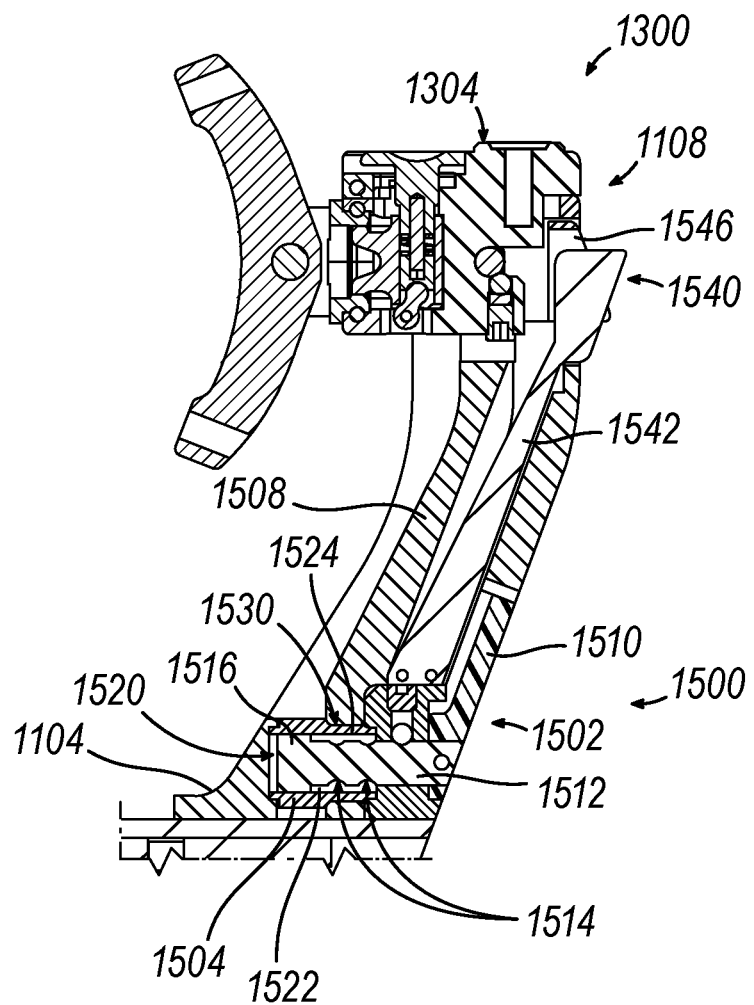
FIG. 11A depicts a cross section view of the arm of FIG. 10.

FIG. 10 illustrates second frame portion (1104) in greater detail. Second frame portion (1104) of the present example includes a tensioning feature (1500). Tensioning feature (1500) of the present example is used to adjust an amount of force HFD (1010) imparts on the patient during use. Tensioning feature (1500) of the present example comprises actuator (1502) and an elongated member (1508) as shown in FIG. 11A. Actuator (1502) is generally configured to adjust the position of elongated member (1508) to thereby adjust the amount of force the connected stabilization assembly (1300) imparts on the patient during use of HFD (1010). As shown, in some examples tensioning feature (1500) is spaced apart with actuator (1502) located some distance away from stabilization assembly (1300). In other words, actuator (1502) of tensioning feature (1500) can be located along a base or lateral portion of frame (1100) as opposed to an upright portion of frame (1100). At the same time, other portions of tensioning feature (1500) that contact stabilization assembly (1300) to adjust pinning force are located some distance away from actuator (1502). In some examples, this spacing may be about the same distance as that represented by a typical patient's head size such that actuator (1502) would not overlap with the lateral regions around the patient's head when positioned within HFD (1010).

FIG. 11A illustrates the configuration of actuator (1502) in greater detail. Actuator (1502) of the present example is generally configured to interact with a body (1504) to selectively engage and disengage rotation of body (1504) via actuator (1502). As will be described in greater detail below, body (1504) is configured to engage a portion of elongated member (1508) or other components associated therewith to drive translation of elongated member (1508) via rotation of body (1504) using actuator (1502).

Suitable selective rotational engagement between actuator (1502) and body (1504) may be accomplished in a variety of ways. By way of example only, actuator (1502) of the present example includes a handle (1510) with an elongated rod (1512) extending into the interior of second frame portion (1104) from handle (1510). The end of elongated rod (1512) opposite handle (1510) includes a keyed end (1516). As will be described in greater detail below, keyed end (1516) is generally configured to engage a portion of body (1504) to provide rotation of body (1504) after actuator (1502) is translated into a predetermined position.

For engagement with actuator (1502), body (1504) includes a hollow interior (1520) configured to receive elongated rod (1512) of actuator (1502). Hollow interior (1520) defines a cylindrical portion (1522) and an engagement portion (1524) oriented toward opposite ends of body (1504). Cylindrical portion (1522) defines a generally cylindrical shape such that keyed end (1516) can freely rotate within cylindrical portion (1522). Meanwhile, engagement portion (1524) defines a shape generally corresponding to the shape of keyed end (1516). Thus, engagement portion (1524) is generally configured to receive keyed end (1516) to thereby form a keyed relationship to permit transfer of rotary motion from elongated rod (1512) to body (1504).

As noted above, actuator (1502) is configured to rotate body (1504) when actuator (1502) is in a predetermined longitudinal position relative to body (1504). Accordingly, and as will be described in greater detail below, actuator (1502) is movable between one or more positions to selectively transition between engagement and disengagement with body (1504) for rotation thereof. To maintain actuator (1502) in a given position relative to body (1504), elongated rod (1512) of actuator includes one or more detent features (1514) extending into the surface of elongated rod (1512). In the present example, elongated rod (1512) includes three semi-circular indentations positioned at three locations along the longitudinal axis of elongated rod (1512). Each detent (1514) feature is configured to engage a spring-loaded bearing, ball, or other resilient feature to thereby releasably hold elongated rod (1512) in a predetermined position along the longitudinal axis of elongated rod (1512). As will be described in greater detail below, this configuration generally permits actuator (1502) to be selectively locked into selected one of a plurality of predetermined positions corresponding to operation of actuator (1502).

Body (1504) defines a generally cylindrical shape. The exterior of body (1504) includes external threading. As will be described in greater detail below, such external threading may be configured to drive elongated member (1508) or other components associated therewith. Body (1504) is secured in position within second frame portion (1104). In particular, the interior geometry of second frame portion (1104) is such that body (1504) is fixed in a single lateral and longitudinal position. However, despite this fixation, body (1504) is still configured to rotate within second frame portion (1104).

Elongated member (1508) is illustrated in greater detail in FIG. 11A. Elongated member (1508) of the present example is generally configured to move to adjust the amount of force the connected stabilization assembly (1300) imparts on the patient during use of HFD (1010). As can be seen, elongated member (1508) extends upwardly from body (1504) toward stabilization assembly (1300). As will be described in greater detail below, at least a portion of elongated member (1508) is in contact with the connected stabilization assembly (1300) to transfer force to stabilization assembly (1300) from body (1504).

Elongated member (1508) is associated with an indicator member (1542). In particular, a lower portion of indicator member (1542) is fastened to a lower portion of elongated member (1508) such that the lower portion of indicator member (1542) and the lower portion of elongated member (1508) are fixedly secured together. Such fixation can be obtained by any suitable means. For instance, in the present example such fixation is obtained using one or more pins.

Indicator member (1542) extends upwardly within second frame portion (1104) independently from elongated member (1508). In other words, indicator member (1542) is only coupled to elongated member (1508) at the lower portion thereof. The remaining portion(s) of indicator member (1542) is not connected to elongated member (1508) such that an upper portion of indicator member (1542) and an upper portion of elongated member (1508) are freely movable relative to each other. As will be described in greater detail below, this configuration is generally configured to permit indicator member (1542) to act as a scale or force indicator for the amount of force applied to the patient's head by stabilization assembly (1300).

Elongated member (1508) includes a threaded opening (1530) on an end opposite of stabilization assembly (1300). Threaded opening (1530) is generally configured to receive body (1504) therein and engage external threads of body (1504). As described above, body (1504) is in a generally fixed position within second frame portion (1104). Thus, by threaded opening (1530) receiving body (1504), the bottom portion of elongated member (1508) is generally likewise secured in a fixed position by body (1504). Additionally, and as will be described in greater detail below, elongated member (1508) is configured to be translated within second frame portion (1104) by rotation of body (1504) and engagement between threads of threaded opening (1530) and body (1504). In other words, body (1540) is configured similar to a lead screw to mechanically ground a portion of elongated member (1508) while also providing translation of elongated member (1508) using rotary input from actuator (1502).

Figure 11B:
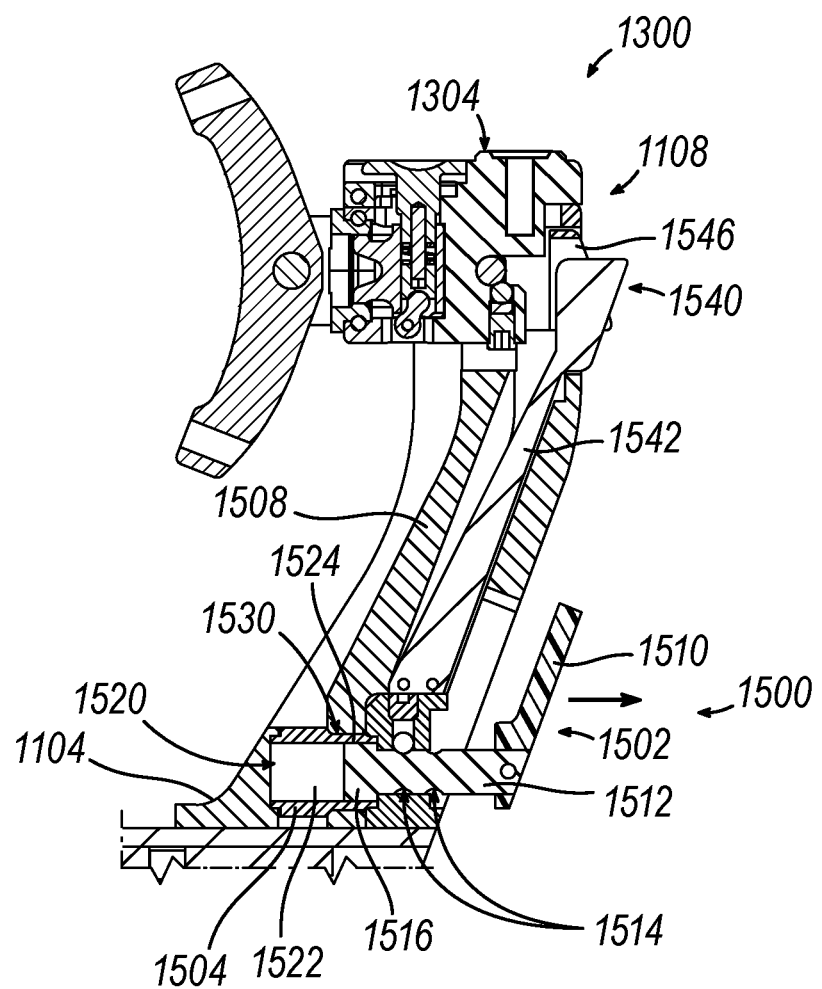
FIG. 11B depicts another cross section view of the arm of FIG. 10, showing an actuator in an actuation configuration.

To adjust tensioning feature (1500), actuator (1502) is first pulled away from second frame portion (1104) as illustrated in FIG. 11B. This pulling motion transitions actuator (1502) from an initial stowed configuration to an actuation configuration. Although not shown, it should be understood that in some examples, actuator (1502) may be configured with an intermediate configuration. In the intermediate configuration, actuator (1502) is freely rotatable without having any effect on tensioning feature (1500). By way of example only, such a configuration may be desirable to permit an operator to adjust the operational position of actuator (1502) prior to use in adjusting tensioning feature (1500).

Figure 11C:
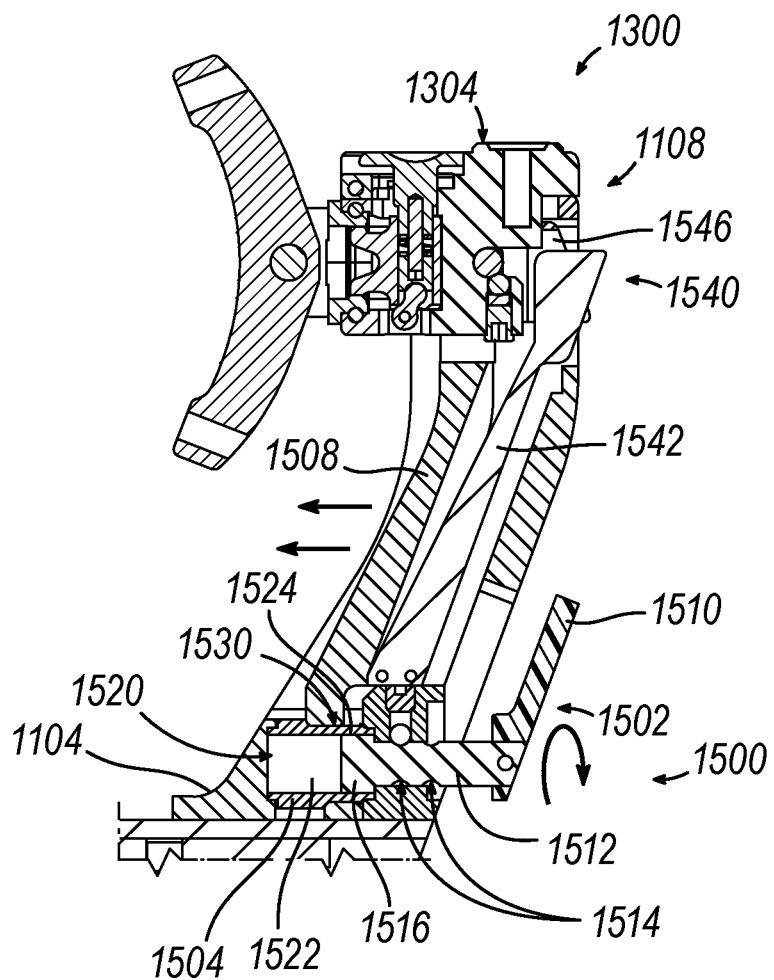
FIG. 11C depicts another cross section view of the arm of FIG. 10, showing the actuator of FIG. 11B used to adjust the tension adjustment feature.

Once actuator (1502) is positioned in the actuation configuration illustrated in FIG. 11B, actuator (1502) is positioned to adjust tensioning feature (1500). As illustrated in FIG. 11C, actuator (1502) may be rotated while in the actuation configuration. This rotation results in corresponding rotation of body (1504). As body (1504) rotates, threads on the exterior of body (1504) engage threads on the interior of threaded opening (1530) of elongated member (1508) to thereby translate elongated member (1508) along the longitudinal axis of body (1504).

In some examples, translation of elongated member (1508) may be visualized using one or more openings or windows within second frame portion (1104). For instance, referring again to FIGS. 9 and 10, second frame portion (1104) includes an opening (1105) configured to permit an operator to visualize movement of elongated member (1508). Opening (1105) of the present example is configured as an elongated slot that receives a pin projecting from elongated member (1508). Thus, pin of elongated member (1508) can progress along the length defined by opening (1105) to show progression of elongated member (1508) along its entire movement path. Although opening (1105) in the present example is configured as an elongate slot, it should be understood that in other examples various alternative configurations may be used such as on oval or square window, a transparent section and/or etc.

The direction of translation of elongated member (1508) depends on the direction of rotation of actuator (1502). Tension is increased, or in other words the force imparted on the patient is increased, when body (1504) is rotated to move elongated member (1508) toward frame portion (1102). Meanwhile, tension is decreased when body (1504) is rotated by actuator (1502) in the opposite direction to move elongated member (1508) away from frame portion (1102).

Figure 12:
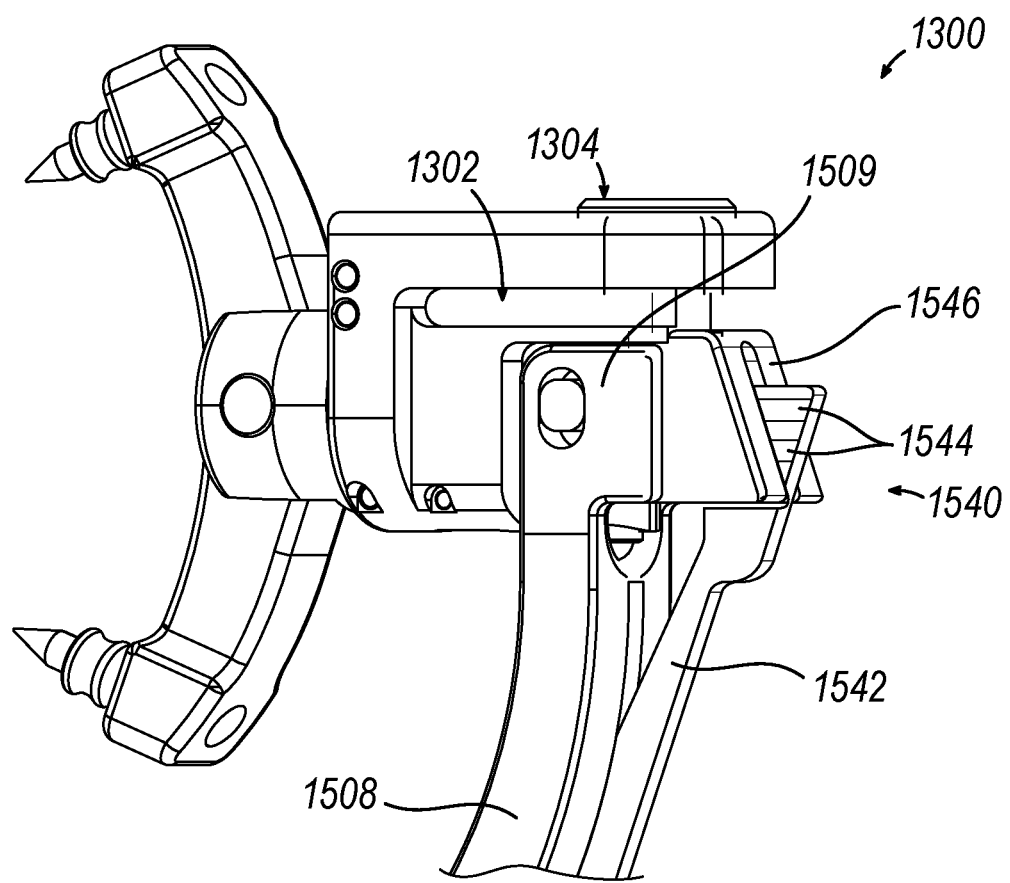
FIG. 12 depicts a side elevational view of an upper portion of the arm of FIG. 10.

As illustrated in FIG. 12, the end of elongated member (1508) opposite body (1504) comprises a pair of extensions (1509) with a space between them. Within this space, stabilization assembly (1300) is positioned and further makes a pinned connection with the pair of extensions (1507). Thus, by moving elongated member (1508) toward first frame portion (1102), elongated member (1508) applies pressure to stabilization assembly (1300) in a direction towards frame portion (1102). Meanwhile, movement of elongated member (1508) away from first frame portion (1102) decreases the pressure applied to stabilization assembly (1300). Also shown in FIG. 12 is one of a pair of slots (1302) incorporated in stabilization assembly (1300). Slots (1302) are on each side of stabilization assembly (1300) and receive a projecting upper portion of second frame portion (1104) such that stabilization assembly (1300) can translate or slide laterally relative to frame portion (1104) in response to force applied by elongated member (1508).

Also shown in FIG. 12 is interface (1304) that is located on top portion of stabilization assembly (1300) and is oriented facing upward in the illustration or away from frame portion (1104). Interface (1304) is configured as a starburst feature in the present example but can be configured in other ways in other versions. Furthermore, various accessories for use in medical procedures such as neurosurgery, etc. are selectively attachable with interface (1304).

Returning to discuss tensioning feature (1500), elongated member (1508) of the present example is configured to bend or flex relative to body (1504). In particular, a patient's head is positionable between frame portions (1102, 1104) with pins of stabilization assemblies (1200, 1300) contacting the patient's head. With the patient in this pinned position, as elongated member (1508) is moved toward first frame portion (1102) as described above to exert a force on stabilization assembly (1300), an opposite force is exerted on elongated member (1508) based on the patient's head being in the pinned position. As a result, elongated member (1508) is configured to bend or flex in the portion of elongated member (1508) extending away from body (1504). Accordingly, this bending or flexing of elongated member (1508) provides a spring force or bending force that is directed to stabilization assembly (1300) and ultimately to the pins contacting the patient such that elongated member (1508) provides a way to adjust the pinning force used with the patient.

Figure 13:
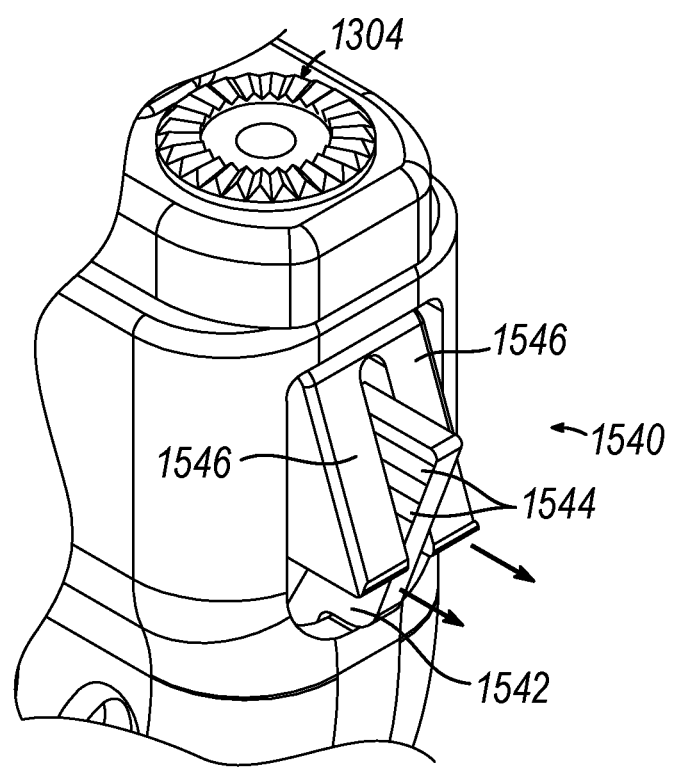
FIG. 13 depicts a perspective view of an exemplary force indicator of the arm of FIG. 10.

Referring to FIG. 13, tensioning feature (1500) of the present example further includes a force indication or scale (1540) associated with elongated member (1508) and indicator member (1542). Scale (1540) is generally configured to correlate the tension within elongated member (1508) based on a force that is applied to stabilization assembly (1300). In general terms, scale (1540) is configured to use relative motion between elongated member (1508) and indicator member (1542) to indicate the tension within elongated member (1508), which correlates with the pinning force applied to the patient. As can be seen, scale (1540) is formed by a plurality of horizontally extending, color coded bars (1544) disposed on the surface of an upper portion of indicator member (1542).

Additionally, elongated member (1508) includes a sloped projection (1546) adjacent to bars (1544) of indicator member (1542). Sloped projection (1546) is generally angled to project away from first frame portion (1102). Consequently, when elongated member (1508) bends or flexes, a corresponding number of bars (1544) are covered or exposed depending on the particular amount of bending or flexion of elongated member (1508) due to relative movement between the upper portion of elongated member (1508) and the upper portion of indicator member (1542). As will be appreciated by the teaching herein, more bending or flexion of elongated member (1508) corresponds to a greater tension on elongated member (1508) and thus greater pinning force on the patient. Thus, for example, where a relatively high tension is applied to elongated member (1508), the upper portion thereof can be moved a greater distance relative to indicator member (1542), thereby covering a greater number of bars (1544) with sloped projection (2546).

As noted above, bars (1544) are color coded to indicate the amount of tension within elongated member (1508). In the present example, the particular color code used is a gradient between orange or yellow (low tension) and red (high tension). In other examples, other suitable color codes may be used as may be apparent to those of ordinary skill in the art in view of the teachings herein. Although the present example is shown as using discrete bars of various colors, in other examples a continuous gradient without separate bars may be used. In addition, or in the alternative, other non-color dependent codes may be used such as numbers or symbols. Also, in some versions no color coding may be used and instead the number of bars visible may be used to indicate the force.

Figure 14:
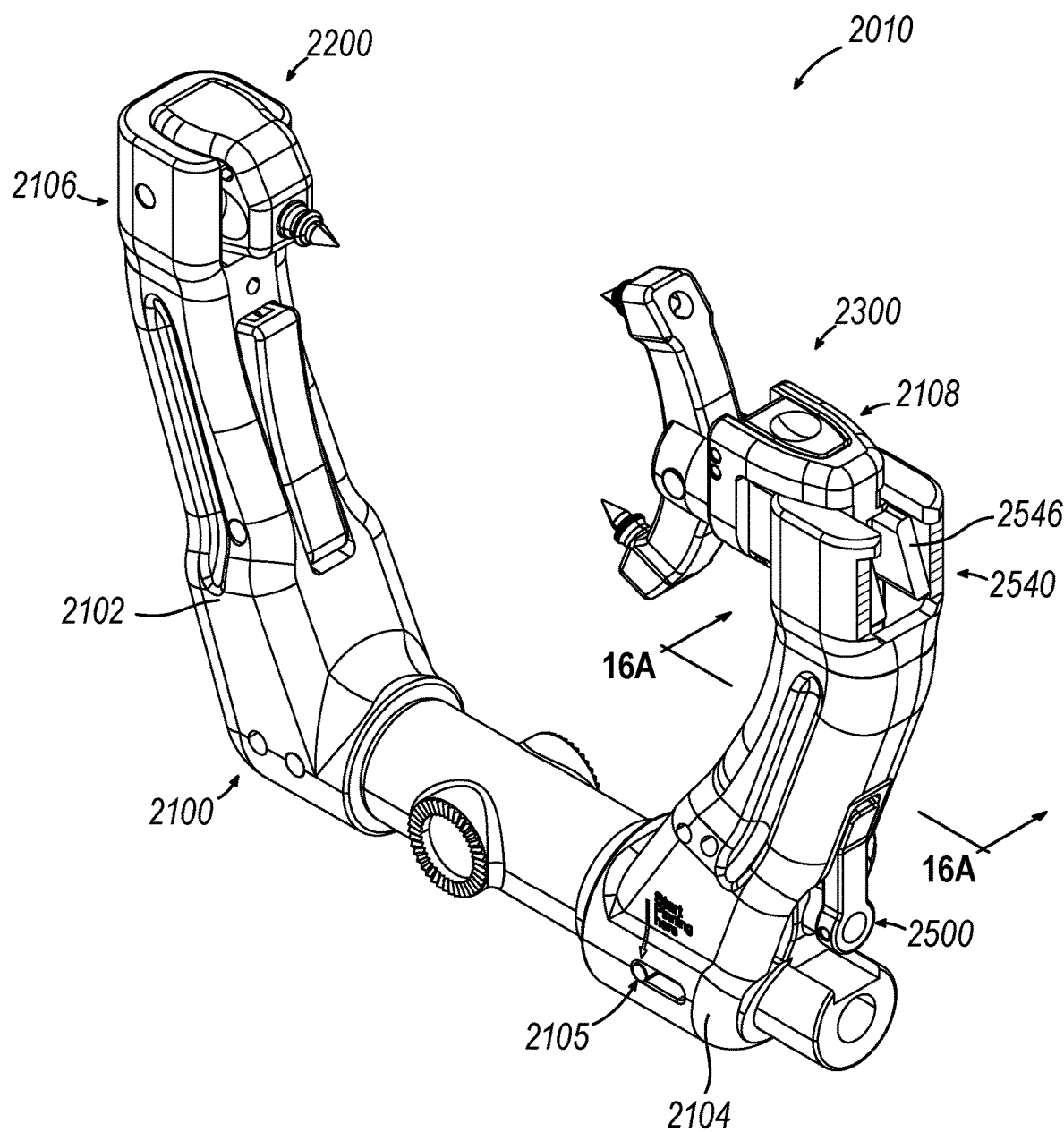
FIG. 14 depicts a perspective view of another exemplary skull clamp.

V. Exemplary Alternate Skull Clamp with Bending Beam and Movable Frame Tensioning Feature FIG. 14 illustrates an exemplary alternative HFD (2010) that is substantially similar to HFDs (10, 1010) described above, except where otherwise explicitly noted herein. For instance, as with HFD (10) described above, HFD (2010) of the present example has the shape or form of a skull clamp. Accordingly, HFD (2010) of the present example comprises a frame (2100) similar to frame (100) described above. Frame (2100) includes a first frame portion (2102) and a second frame portion (2104). Frame portions (2102, 2104) are adjustably connectable to adjust a spacing between them. Frame portions (2102, 2104) include respective receiving portions (2106, 2108) that are configured to receive a stabilization assembly. In the illustrated version, stabilization assembly (2200) is received by receiving portion (2106) of frame portion (2102). Furthermore, stabilization assembly (2300) is received by receiving portion (2108) of frame portion (2104).

As with HFDs (10, 1010) described above, HFD (2010) of the present example further includes a frame adjustment feature that is operable to adjust the relative spacing between frame portions (2102, 2104). In some versions, the frame adjustment feature may be the same or similar to frame adjustment feature (400) or frame adjustment features (1400) described above. In other examples, various alternative frame adjustment features may be readily incorporated into HFD (2010) or HFDs (10, 1010) for that matter as will be appreciated by those of ordinary skill in the art in view of the teachings herein.

As with HFD (10) described above, HFD (2010) of the present example is configured with a modular design such that receiving portions (2106, 2108) are configured to receive a variety of stabilization assemblies as opposed to only a single type or design of stabilization assembly. As similarly described above, stabilization assembly (2200) and stabilization assembly (2300) could be switched with one another such that stabilization assembly (2200) connects with receiving portion (2108) and similarly stabilization assembly (2300) connects with receiving portion (2106). In this manner, the modularity and interchangeability with respect to stabilization assemblies (2200, 2300) and HFD (2010) operates in the same or similar manner as described above with respect to stabilization assemblies (200, 300) and HFD (10).

Figure 15:
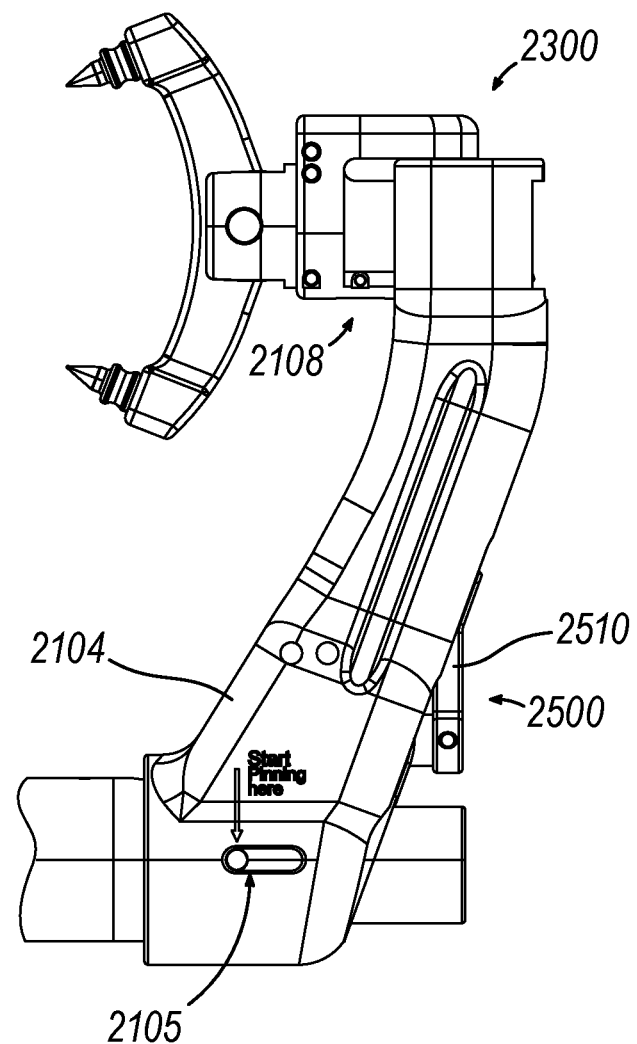
FIG. 15 depicts a side elevational view of an arm of the skull clamp of FIG. 14, showing another alternative tension adjustment feature.

FIG. 15 illustrates second frame portion (2104) in greater detail. As with second frame portions (104, 1104) described above, second frame portion (2104) of the present example includes a tensioning feature (2500). Tensioning feature (2500) of the present example is used to adjust an amount of force the connected stabilizing assembly (2300) imparts on the patient during use of HFD (2010). Tensioning feature (2500) of the present example comprises actuator (2502) and an elongated member (2508). Actuator (2502) is generally configured to adjust the position of elongated member (2508) to thereby adjust the amount of force the connected stabilization assembly (2300) imparts on the patient during use of HFD (2010). However, unlike actuator (1500) discussed above, actuator (2502) of the present example adjusts the position of elongated member (2508) by adjusting the position of second frame portion (2104) and elongated member (2508) rather than only adjusting the position of elongated member (2508).

Figure 16A:
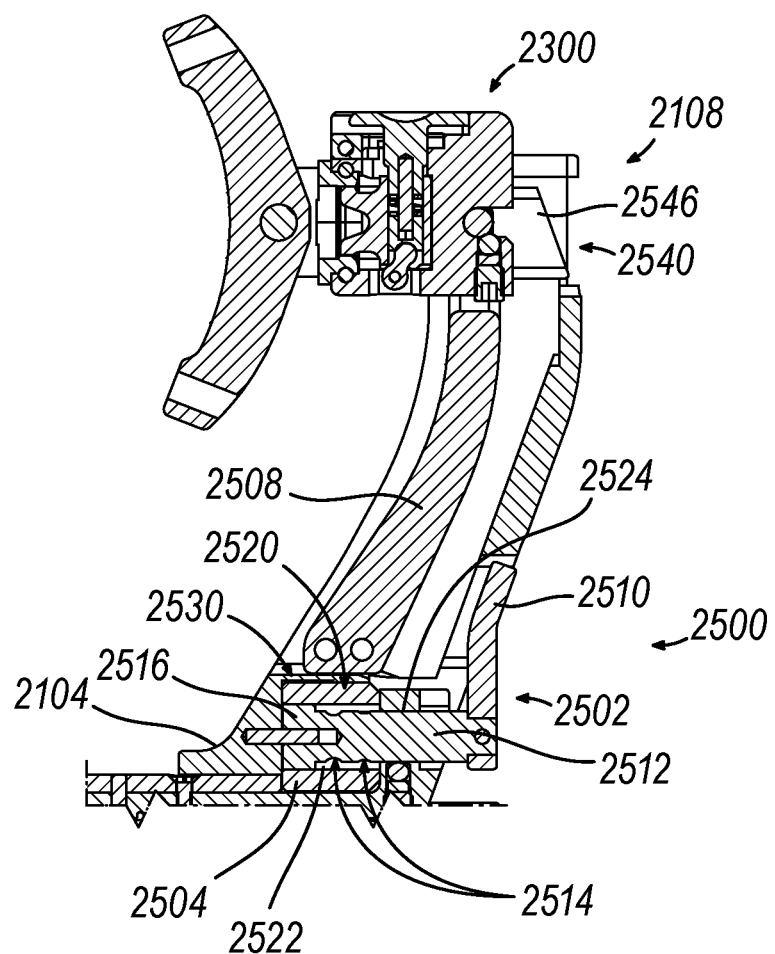
FIG. 16A depicts a cross section view of the arm of FIG. 15.

FIG. 16A illustrates the configuration of actuator (2502) in greater detail. Actuator (2502) of the present example is generally configured to interact with a body (2504) to selectively engage and disengage rotation of body (2504) via actuator (2502). As will be described in greater detail below, body (2504) is configured to engage a portion of second frame portion (2104) or other components associated therewith to drive translation of second frame portion (2104) together with elongated member (2508) via rotation of body (2504) using actuator (2502).

Suitable selective rotational engagement between actuator (2502) and body (2504) may be accomplished in a variety of ways. By way of example only, actuator (2502) of the present example includes a handle (2510) with an elongated rod (2512) extending into the interior of second frame portion (2104) from handle (2510). The end of elongated rod (2512) opposite handle (2510) includes a keyed end (2516). As will be described in greater detail below, keyed end (2516) is generally configured to engage a portion of body (2504) to provide rotation of body (2504) after actuator (2502) is translated into a predetermined position.

For engagement with actuator (2502), body (2504) includes a hollow interior (2520) configured to receive elongated rod (2512) of actuator (2502). Hollow interior (2520) defines a cylindrical portion (2522) and an engagement portion (2524) oriented toward opposite ends of body (2504). Cylindrical portion (2522) defines a generally cylindrical shape such that keyed end (2516) can freely rotate within cylindrical portion (2522). Meanwhile, engagement portion (2524) defines a shape generally corresponding to the shape of keyed end (2516). Thus, engagement portion (2524) is generally configured to receive keyed end (2516) to thereby form a keyed relationship to permit transfer of rotary motion from elongated rod (2512) to body (2504).

As noted above, actuator (2502) is configured to rotate body (2504) when actuator (2502) is in a predetermined longitudinal position relative to body (2504). Accordingly, and as will be described in greater detail below, actuator (2502) is movable between one or more positions to selectively transition between engagement and disengagement with body (2504) for rotation thereof. To maintain actuator (2502) in a given position relative to body (2504), elongated rod (2512) of actuator includes one or more detent features (2514) extending into the surface of elongated rod (2512). In the present example, elongated rod (2512) includes three semi-circular indentations positioned at three locations along the longitudinal axis of elongated rod (2512). Each detent (2514) feature is configured to engage a spring-loaded bearing, ball, or other resilient feature to thereby releasably hold elongated rod (2512) in a predetermined position along the longitudinal axis of elongated rod (2512). As will be described in greater detail below, this configuration generally permits actuator (2502) to be selectively locked into selected one of a plurality of predetermined positions corresponding to operation of actuator (2502).

Body (2504) defines a generally cylindrical shape, and the exterior of body (2504) includes external threading. As will be described in greater detail below, such external threading may be configured to drive second frame portion (2104) and/or other components associated therewith. Body (2504) is secured in position within a portion of frame (2100). In particular, the interior geometry of a lower portion of frame (2100) is such that body (2504) is fixed in a single lateral and longitudinal position. However, despite this fixation, body (2504) is still configured to rotate relative to second frame portion (2106).

Elongated member (2508) is illustrated in greater detail in FIG. 16A. Elongated member (2508) of the present example is generally configured to move to adjust the amount of force the connected stabilization assembly (2300) imparts on the patient during use of HFD (2010). As can be seen, elongated member (2508) extends upwardly from body (2504) toward stabilization assembly (2300). As will be described in greater detail below, at least a portion of elongated member (2508) is in contact with the connected stabilization assembly (2300) to transfer force to stabilization assembly (2300) from body (2504).

Elongated member (2508) is generally pinned to a portion of second frame portion (2104). In particular, one or more pins secure a lower portion of elongated member (2508) to a lower portion of second frame portion (2104). Consequently, it should be understood that movement of second frame portion (2104) results in corresponding movement of at least the lower portion of elongated member (2508), as will be discussed in greater detail below.

Second frame portion (2104) includes a threaded bore (2530) proximate the lower portion of second frame portion (2104). Threaded bore (2530) is generally configured to receive body (2504) therein and engage external threads of body (2504). As described above, body (2504) is in a generally fixed position relative to a lower portion of frame (2100). Thus, by threaded bore (2530) receiving body (2504), second frame portion (2104) is generally likewise secured in a fixed position by body (2504). Because the lower portion of elongated member (2508) is secured to second frame portion (2104), the lower portion of elongated member (2508) is likewise secured in a fixed position by body (2504). Additionally, and as will be described in greater detail below, elongated member (2508) is configured to be translated by second frame portion (2104) using rotation of body (2504) and engagement between threads of threaded bore (2530) and body (2504). In other words, body (2540) is configured similar to a lead screw to mechanically ground a portion of second frame portion (2104) and elongated member (2508) while also providing translation of second frame portion (2104) and elongated member (2508) using rotary input from actuator (2502).

Figure 16B:
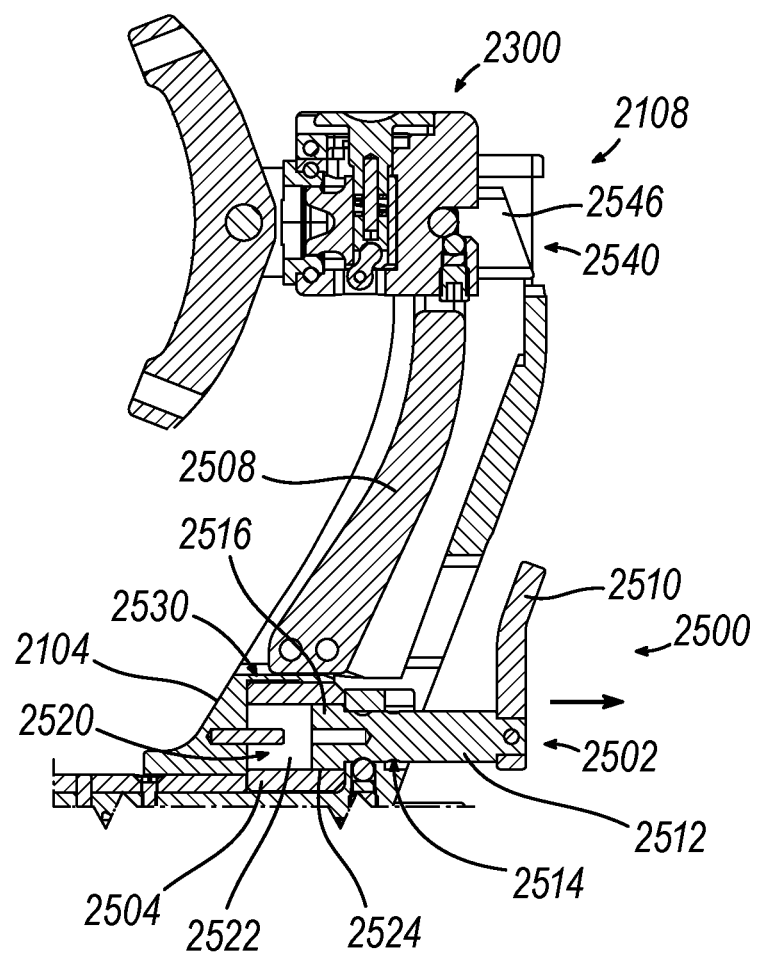
FIG. 16B depicts another cross section view of the arm of FIG. 15, showing an actuator in an actuation configuration.

To adjust tensioning feature (2500), actuator (2502) is first pulled away from second frame portion (2104) as illustrated in FIG. 16B. This pulling motion transitions actuator (2502) from an initial stowed configuration to an actuation configuration. It should be understood that in some examples, actuator (2502) may be configured with an intermediate configuration. In the intermediate configuration, actuator (2502) is freely rotatable without having any effect on tensioning feature (2500). By way of example only, such a configuration may be desirable to permit an operator to adjust the operational position of actuator (2502) prior to use in adjusting tensioning feature (2500).

Figure 16C:
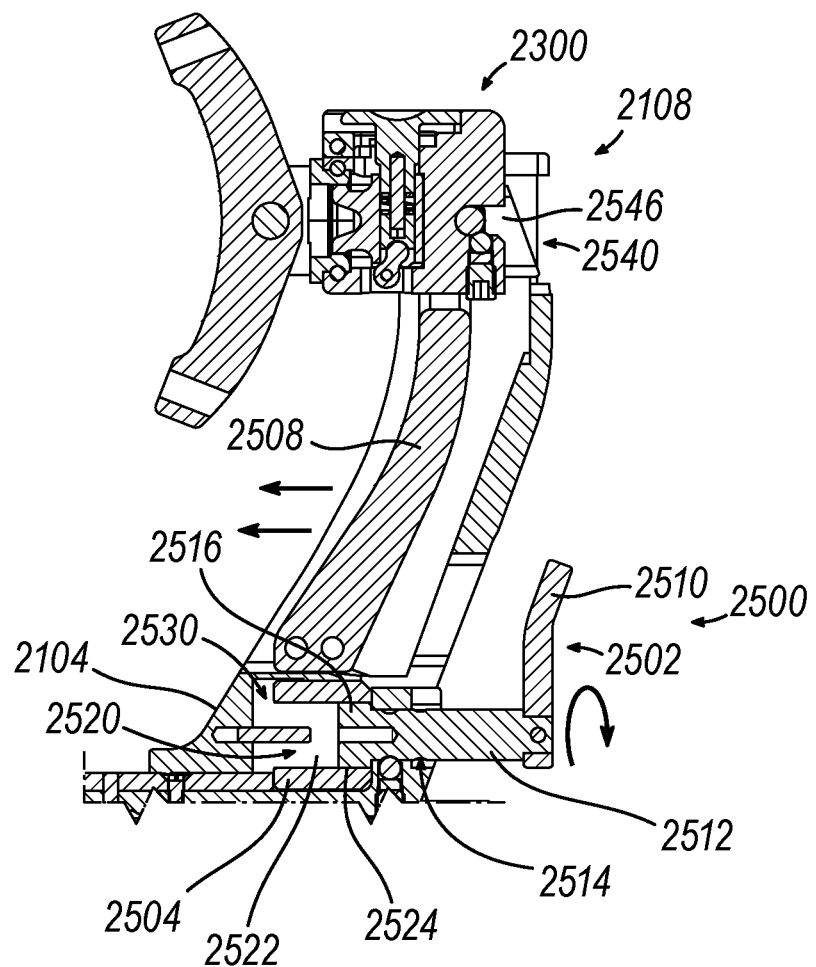
FIG. 16C depicts another cross section view of the arm of FIG. 15, showing the actuator of FIG. 16B used to adjust the tension adjustment feature.

Once actuator (2502) is positioned in the actuation configuration illustrated in FIG. 16B, actuator (2502) is positioned to adjust tensioning feature (2500). As illustrated in FIG. 16C, actuator (2502) may be rotated while in the actuation configuration. This rotation results in corresponding rotation of body (2504). As body (2504) rotates, threads on the exterior of body (2504) engage threads on the interior of threaded bore (2530) of second frame portion (2104) to thereby translate second frame portion (2104) along the longitudinal axis of body (2504). Simultaneously, translation of second frame portion (2104) results in corresponding translation of at least the bottom portion of elongated member (2508) along the longitudinal axis of body (2504).

In some examples, translation of second frame portion (2104) and elongated member (2508) may be visualized using one or more openings or windows within second frame portion (2104). For instance, referring again to FIGS. 14 and 15, second frame portion (2104) includes an opening (2105) configured to permit an operator to visualize movement of second frame portion (2104) and elongated member (2508). Opening (2105) of the present example is configured as an elongated slot that receives a pin projecting from a lower portion of frame (2100). Thus, pin of the lower portion of frame (2100) can progress along the length defined by opening (2105) to show progression of second frame portion (2104) and elongated member (2508) along their entire movement path. Although opening (2105) in the present example is configured as an elongate slot, it should be understood that in other examples various alternative configurations may be used such as on oval or square window, a transparent section and/or etc.

The direction of translation of second frame portion (2104) and elongated member (2508) depends on the direction of rotation of actuator (2502). Tension is increased, or in other words the force imparted on the patient is increased, when body (2504) is rotated to move second frame portion (2104) and elongated member (2508) toward first frame portion (2102). Meanwhile, tension is decreased when body (2504) is rotated by actuator (2502) in the opposite direction to move second frame portion (2104) and elongated member (2508) away from first frame portion (2102).

Figure 17:
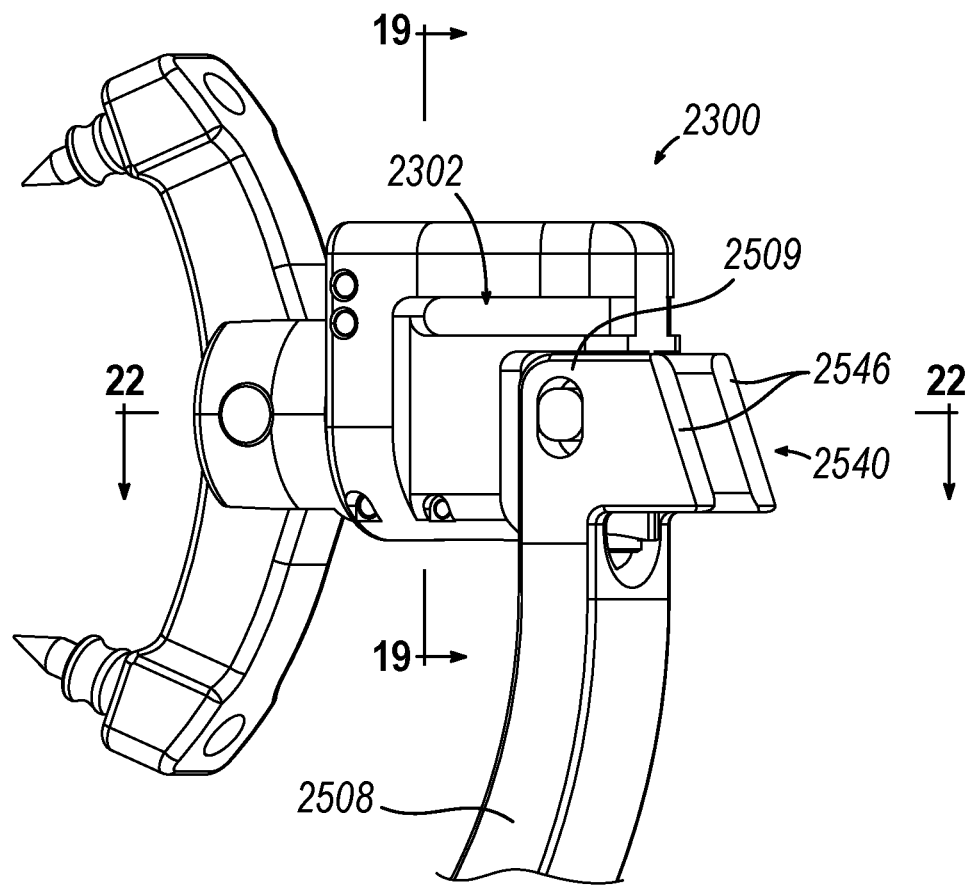
FIG. 17 depicts a side elevational view of an upper portion of the arm of FIG. 15.

As illustrated in FIG. 17, the end of elongated member (2508) opposite body (2504) comprises a pair of extensions (2509) with a space between them. Within this space, stabilization assembly (2300) is positioned and further makes a pinned connection with the pair of extensions (2507). Thus, by moving elongated member (2508) toward first frame portion (2102), elongated member (2508) applies pressure to stabilization assembly (2300) in a direction towards frame portion (2102). Meanwhile, movement of elongated member (2508) away from first frame portion (2102) decreases the pressure applied to stabilization assembly (2300). Also shown in FIG. 17 is one of a pair of slots (2302) incorporated in stabilization assembly (2300). Slots (2302) are on each side of stabilization assembly (2300) and receive a projecting upper portion of second frame portion (2104) such that second frame portion (2104) can translate or slide laterally relative to stabilization assembly (2300).

Elongated member (2508) of the present example is configured to bend or flex relative to body (2504). In particular, a patient's head is positionable between frame portions (2102, 2104) with pins of stabilization assemblies (2200, 2300) contacting the patient's head. With the patient in this pinned position, as elongated member (2508) is moved toward first frame portion (2102) as described above to exert a force on stabilization assembly (2300), an opposite force is exerted on elongated member (2508) based on the patient's head being in the pinned position. As a result, elongated member (2508) is configured to bend or flex in the portion of elongated member (2508) extending away from body (2504). Accordingly, this bending or flexing of elongated member (2508) provides a spring force or bending force that is directed to stabilization assembly (2300) and ultimately to the pins contacting the patient such that elongated member (2508) provides a way to adjust the pinning force used with the patient.

Figure 18:
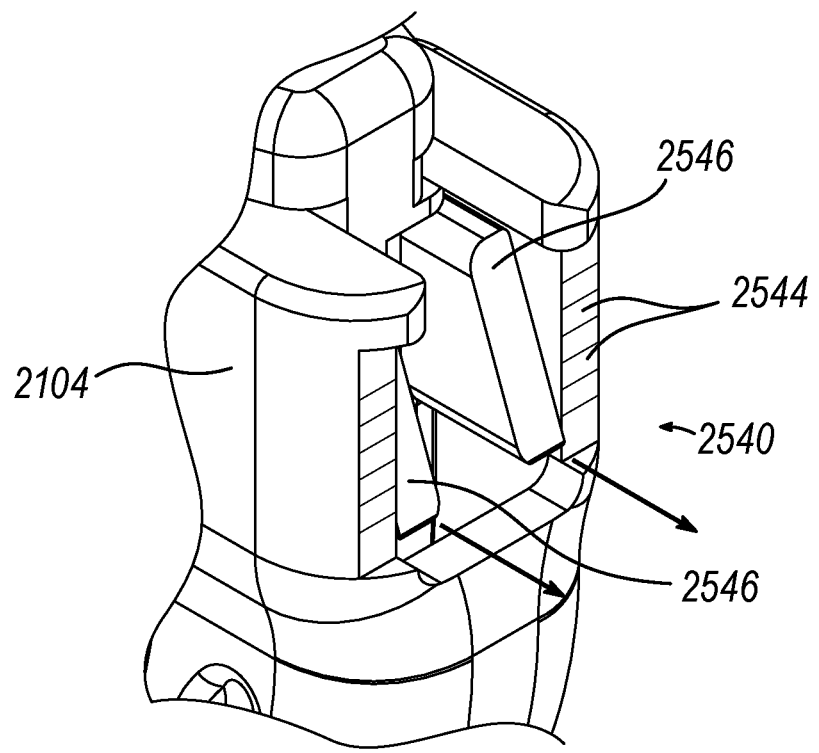
FIG. 18 depicts a perspective view of an exemplary force indicator of the arm of FIG. 15.

Referring to FIG. 18, tensioning feature (2500) of the present example further includes a force indication or scale (2540) associated with elongated member (2508). Scale (2540) is generally configured to correlate the tension within elongated member (2508) based on a force that is applied to stabilization assembly (2300). In general terms, scale (2540) is configured to use relative motion between elongated member (2508) and an upper portion of second frame portion (2104) to indicate the tension within elongated member (2508), which correlates with the pinning force applied to the patient. As can be seen, scale (2540) is formed by a plurality of horizontally extending, color coded bars (2544) disposed on the surface of the upper portion of second frame portion (2104).

Additionally, elongated member (2508) includes a sloped projection (2546) adjacent to bars (2544) of second frame portion (2104). Sloped projection (2546) is generally angled to project away from first frame portion (2102). Consequently, when elongated member (2508) bends or flexes, sloped projection (2544) is moved to intersect with, point to, or otherwise align with, a given bar (2544) of bars (2544) depending on the particular amount of bending or flexion of elongated member (2508) due to relative movement between the upper portion of elongated member (2508) and the upper portion of second frame portion (2104). As will be appreciated by the teachings herein, more bending or flexion of elongated member (2508) corresponds to a greater tension on elongated member (2508) and thus greater pinning force on the patient. Thus, for example, where a relatively high tension is applied to elongated member (2508), the upper portion thereof can be moved a greater distance relative to second frame portion (2104), thereby moving sloped projection (2546) into alignment with a bar (2544) higher on the scale defined by bars (2544).

As noted above, bars (2544) are color coded to indicate the amount of tension within elongated member (2508). In the present example, the particular color code used is a gradient between orange or yellow (low tension) and red (high tension). In other examples, other suitable color codes may be used as may be apparent to those of ordinary skill in the art in view of the teachings herein. Although the present example is shown as using discrete bars of various colors, in other examples a continuous gradient without separate bars may be used. In addition, or in the alternative, other non-color dependent codes may be used such as numbers or symbols. Also, in some versions no color coding may be used and instead the number of bars visible may be used to indicate the force.

VI. Exemplary Rocker Arm Locking Feature

Figure 19:
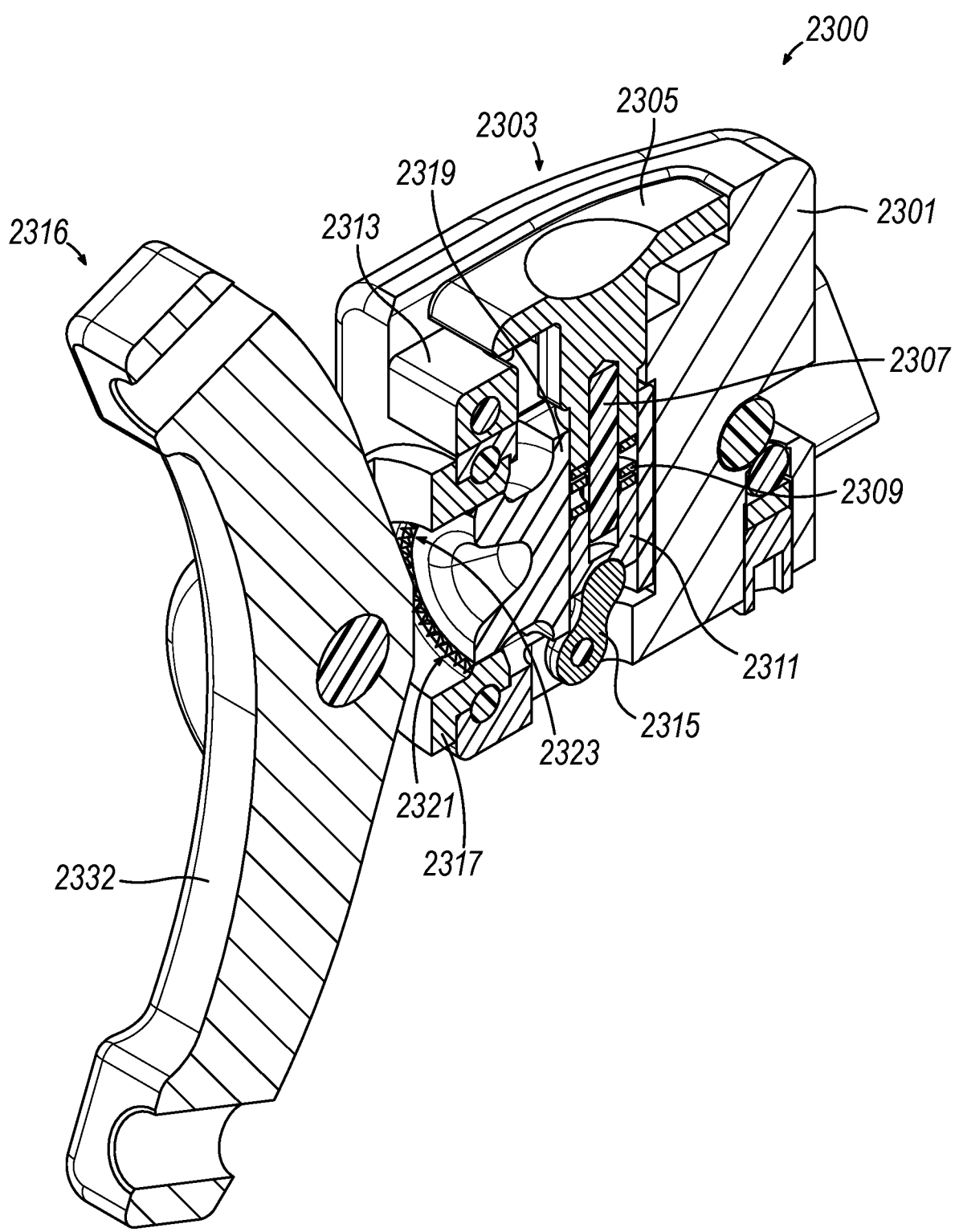
FIG. 19 depicts a perspective view in cross section of an exemplary stabilization assembly of the skull clamp of FIG. 14 shown with an exemplary rocker arm assembly rotationally fixed.
Figure 20:
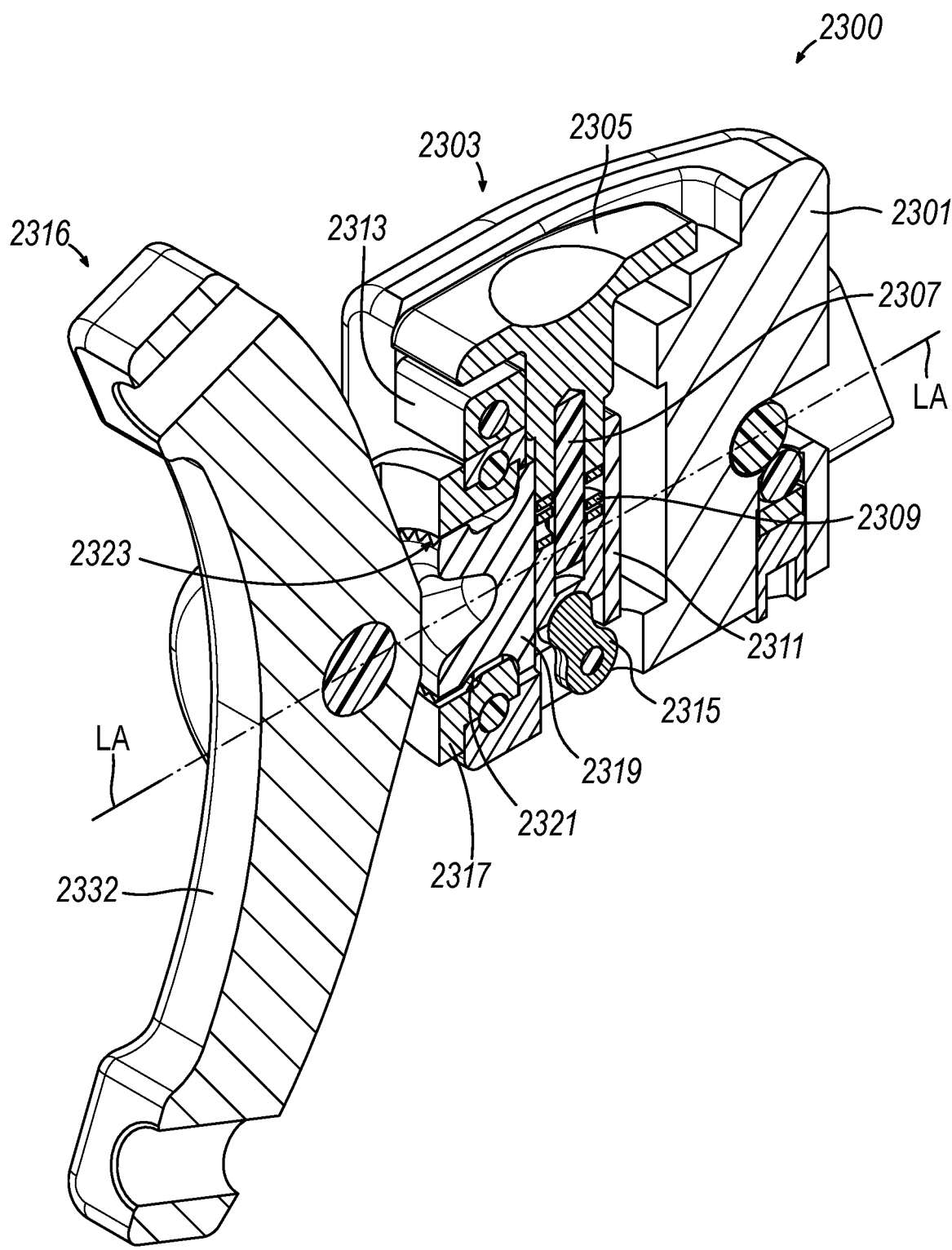
FIG. 20 depicts a perspective view in cross section of the exemplary stabilization assembly of FIG. 19, shown with the exemplary rocker arm assembly rotationally adjustable.

Another feature of HFDs (1010, 2010) pertains to a locking feature of stabilization assemblies (1300, 2300). FIGS. 19 and 20 illustrate a perspective sectioned view of stabilization assembly (2300). The locking feature components and operability is the same with stabilization assembly (1300) as with stabilization (2300). For conciseness, the locking feature will be described with respect to FIGS. 19 and 20 illustrating stabilization assembly (2300), but it being understood that the description applies equally to stabilization assembly (1300).

Now referring to FIGS. 19 and 20, the locking feature allows for selective rotational adjustment of the rocker arm assembly (2316) relative to the respective housing (2301) of stabilization assembly (2300). Stabilization assembly (2300) comprises an actuator (2303) that includes a key or depressible member (2305), a pin (2307), a spring (2309), a spring seat (2311), an inset member (2313), and a lever (2315). Rocker arm assembly (2316) comprises a holder (2317) that has a pinned connection with rocker arm (2332). Stabilization assembly (2300) further comprises a locking member (2319).

In the state depicted in FIG. 19, rocker arm assembly (2316) is in a locked state or position. For instance, holder (2317) has a gear or toothed ring (2321) that in the present example is formed in an interior of holder (2317). Toothed ring (2321) has a plurality of teeth oriented radially about a longitudinal axis passing through an interior bore of holder (2317). In other words, in the present example the plurality of teeth making up toothed ring (2321) extend circumferentially about a surface of holder (2317). To establish the locking state, toothed ring (2321) engages with a gear or toothed ring (2323) of locking member (2319). In this state with toothed rings (2321, 2323) engaged, rocker arm assembly (2316) is rotationally fixed relative to housing (2301).

FIG. 20 depicts rocker arm assembly (2316) in an adjustable or unlocked state or position. In this state, toothed rings (2321, 2323) are separated from one another such that there is no engagement of the respective teeth of toothed rings (2321, 2323). More specifically, as shown in FIG. 20, holder (2317) defines a longitudinal axis (LA), and toothed ring (2323) of locking member (2319) is offset from toothed ring (2321) of holder (2317) toward rocker arm (2332). This offset can similarly be described as toothed rings (2321, 2323) being in different translational positions along longitudinal axis (LA). Without engagement of toothed rings (2321, 2323) as shown in FIG. 20, rocker arm assembly (2316) is rotationally adjustable relative to housing (2301).

Figure 22:
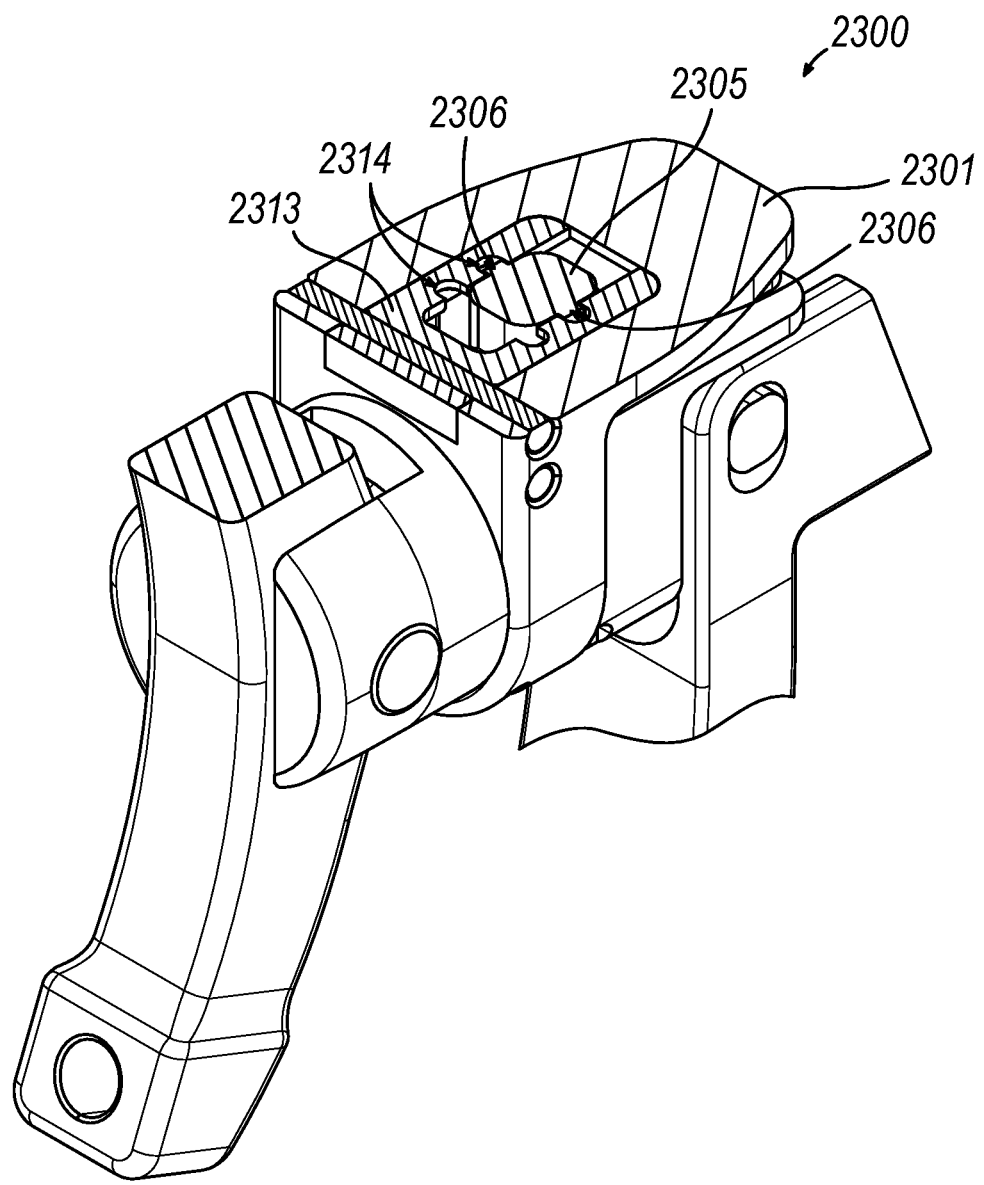
FIG. 22 depicts a perspective view in cross section of the exemplary stabilization assembly of FIG. 14.

To move stabilization assembly (2300) between the locked and unlocked, or fixed and adjustable, states and vice versa, a user depresses key (2305) thereby compressing spring (2309) against seat (2311). With key (2305) depressed, key (2305) is translatable relative to fixed inset member (2313). When key (2305) is not depressed, as shown in FIG. 22, key (2305) includes a protruding feature (2306) that engages with a slot (2314) of inset member (2313) such that key (2305) is translationally locked relative to inset member (2313). For instance, as shown in FIGS. 19 and 20, key (2305) is raised or not depressed such that key (2305) is translationally fixed relative to inset member (2313). To accommodate key (2305) in either position shown in FIGS. 19 and 20, inset member (2313) comprise two or more slots (2314). Key (2305) can also include multiple protruding features (2306) as shown in FIG. 22.

Continuing the example of moving between the fixed state shown in FIG. 19 and the adjustable state shown in FIG. 20, after depressing key (2305), key (2305) is advanced or translated toward rocker arm (2332). Moving with key (2305) are pin (2307), spring (2309), seat (2311), locking member (2319), and lever (2315). As shown in the comparison of FIGS. 19 and 20, lever (2315) has a rotational movement about its pinned connection with housing (2301) while key (2305), pin (2307), spring (2309), seat (2311), and locking member (2319) have a translational movement. With key (2305) and toothed ring (2323) of locking member (2319) now advanced toward rocker arm (2332) as shown in FIG. 20, depressing key (2305) stops and key (2305) returns to its neutral position based on the bias from spring (2309). As mentioned above the protruding member on key (2305) then engages with a corresponding slot of inset member (2313) to fix the translational position of key (2305) and its associated components.

As described above, stabilization assembly (2300) is configured so that an actuator (2303) can be moved between a first position and a second position where in the first position rocker arm assembly (2316) is rotatably fixed, while in the second position rocker arm assembly (2316) is rotatably adjustable. Furthermore, in the present version, based on the engagement of key (2305) with inset member (2313), it is not required for a user to hold key (2305) in a depressed or translated position to adjust or fix rocker arm assembly (2316). This configuration permits the user to setup stabilizing assembly (2300) in a desired position and then lock the rotational position of rocker arm assembly (2316). Additionally, as described above, the action used for moving stabilization assembly between adjustable rocker arm assembly and fixed rocker arm assembly states is achieved with translational movement of radially oriented toothed rings (2321, 2323).

Figure 21:
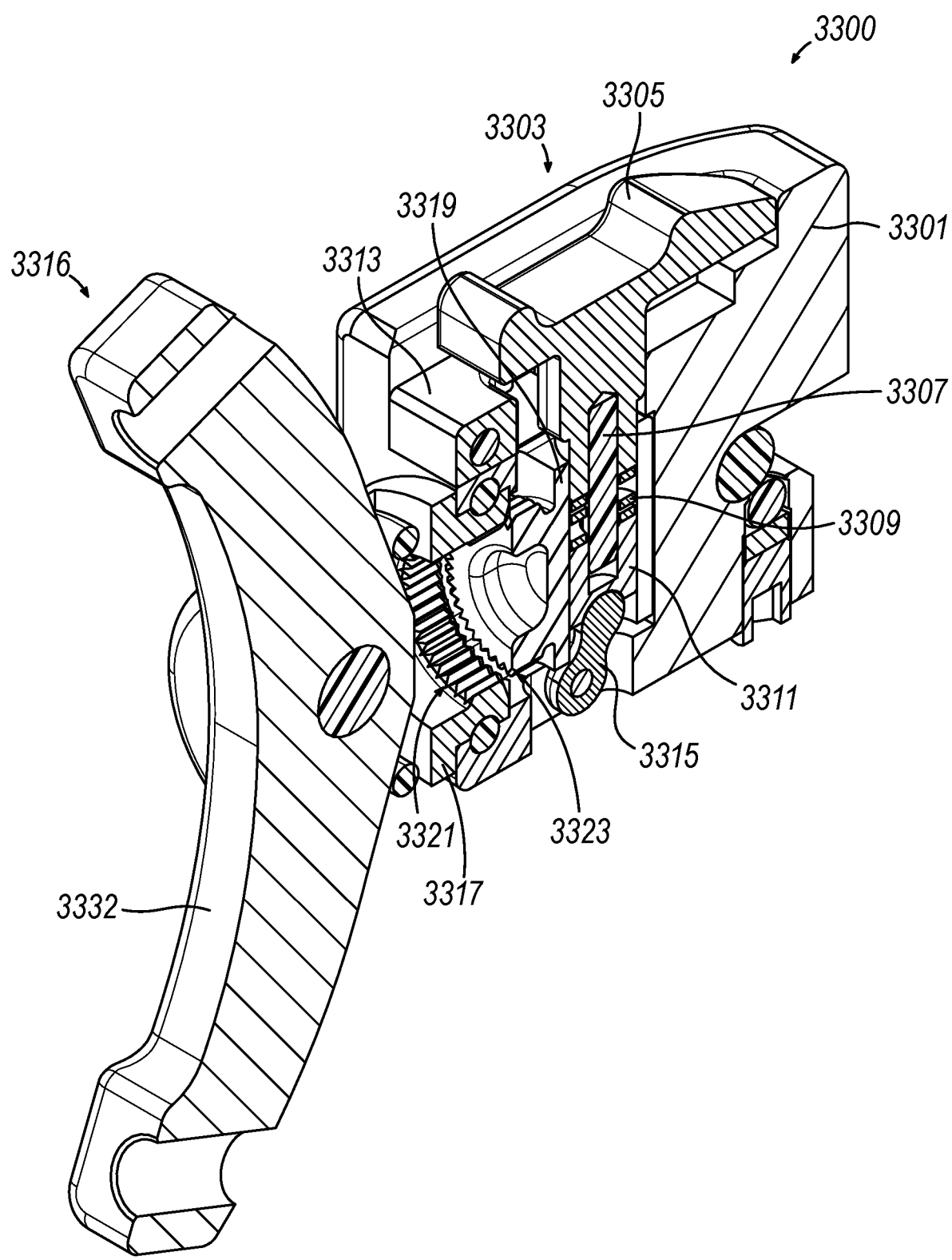
FIG. 21 depicts a perspective view in cross section of another exemplary stabilization assembly usable with the skull clamps of FIGS. 9 and 14, shown with an exemplary rocker arm assembly rotationally adjustable.

In view of the teaching herein, other ways to configure stabilization assembly (2300) or other stabilization assemblies to adjust a rotational position of a rocker arm assembly will be apparent to those of ordinary skill in the art. By way of example only, FIG. 21 illustrates another exemplary stabilization assembly (3300) usable with HFDs (1010, 2010) in place of stabilization assemblies (1300, 2300). Stabilization assembly (3300) comprises actuator (3303) with key (3305), pin (3307), spring (3309), seat (3311), inset member (3313), and lever (3315). Stabilization assembly also comprises locking member (3319) with toothed ring (3323), while rocker arm assembly (3316) comprises holder (3317) with toothed ring (3321). These components of stabilization assembly (3300) are operable in the same manner as described above with respect to their similar counterpart components of stabilization assembly (2300) as shown in FIGS. 19 and 20.

However, a difference between stabilization assembly (3300) and stabilization assembly (2300) is that with stabilization assembly (3300), advancing key (3305) toward rocker arm (3332) moves toothed ring (3323) of locking member (3319) into engagement with toothed ring (3321) of holder (3317) to fix rocker arm assembly (3316) relative to housing (3301). This is the opposite movement or direction of movement described above with respect to stabilization assembly (2300). Similarly, with stabilization assembly (3300), to adjust rocker arm assembly (3316), locking member (3319) is retracted or translated away from rocker arm (3332) to disengage toothed regions (3321, 3323) as seen in FIG. 21.

Again, in view of the teachings herein, other ways to modify stabilization assemblies (1300, 2300, 3300) to achieve a locking feature for the selective adjustment of the rotational position of an associated rocker arm assembly will be apparent to those of ordinary skill in the art.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A device for stabilizing a patient comprising: (a) a stabilization assembly configured to receive a stabilization feature, the stabilization feature being configured to contact the patient; and (b) a tensioning feature configured to receive the stabilization assembly at a first location, the tensioning feature further includes a second location spaced a distance away from the first location such that the second location is spaced away from the stabilization assembly, the tensioning feature including an actuator positioned at the second location such that the actuator is spaced away from the stabilization assembly, the tensioning feature including an elongated member extending from the actuator to the stabilization assembly, the actuator configured to cause movement of the elongate member relative to the stabilization assembly when the stabilization feature is in contact with the patient to adjust an amount of force the stabilization assembly imparts onto the patient.

Example 2

The device of Example 1, at least a portion of the elongated member being configured to bend in response to an increase in force imparted to the stabilization assembly.

Example 3

The device of any one or more of Example 1 through Example 2, the actuator having a body, the actuator configured to transmit rotary motion to the body, the body having a cylindrical portion including threading, the threading being configured to engage threading of the elongated member to move the elongated member relative to the body.

Example 4

The device of any one or more of Example 1 through Example 2, further comprising a frame assembly having a first frame portion and a second frame portion, the actuator having a body, the actuator configured to transmit rotary motion to the body, the body having a cylindrical portion including threading, the threading being configured to engage threading of the second frame portion to move the second frame portion and the elongated member relative to the first frame portion.

Example 5

The device of any one or more of Example 1 through Example 4, the actuator further comprising a rod and a lock feature configured to releasably hold the rod in a selected position of a plurality of predetermined positions relative to the body.

Example 6

The device of any one or more of Example 1 through Example 5, further comprising a force indication feature configured to indicate the amount of force the stabilization assembly imparts onto the patient.

Example 7

The device of Example 6, the force indication feature including a plurality of indicators, wherein the elongated member is movable relative to the plurality of indicators to indicate the amount of force the stabilization assembly imparts onto the patient.

Example 8

The device of any one or more of Example 1 through Example 3, further comprising a frame assembly comprising a first frame portion and a second frame portion, the first and second frame portions are selectively movable relative to one another to adjust a space between the first and second frame portions.

Example 9

The device of Example 8, the tensioning feature being configured to adjust the amount of force the stabilization assembly imparts onto the patient while maintaining the relative position of the first and second frame portions such that the space between the first and second frame portions is unchanged.

Example 10

The device of Example 8, the tensioning feature being configured to adjust the amount of force the stabilization assembly imparts onto the patient while the relative position of the first and second frame portions changes as the amount of force the stabilization assembly imparts onto the patient is adjusted such that the space between the first and second frame portions is changed.

Example 11

The device of any one or more of Example 1 through Example 2, wherein the tensioning feature comprises a body, wherein the actuator is configured to move the elongated member relative to the body to transfer a force to the elongated member, and wherein the elongated member is configured to transfer at least a portion of the force to the stabilization assembly to increase the amount of force the stabilization assembly imparts onto the patient.

Example 12

The device of any one or more of Example 1 through Example 3, further comprising a frame assembly comprising a first frame portion and a second frame portion, and an adjustment feature configured to adjust the relative position of the first and second frame portions to overcome the force applied to the stabilization assembly by the tensioning feature.

Example 13

The device of any one or more of Example 1 through Example 12, wherein the tensioning feature comprises a torsion rod, wherein a torque on the torsion rod transfers a force to the elongated member, and wherein the elongated member transfers at least a portion of the force to the stabilization assembly to increase the amount of force the stabilization assembly imparts onto the patient.

Example 14

The device of any one or more of Example 1 through Example 13, wherein the tensioning feature is configured to apply the amount of force to the stabilization assembly via a twisting action.

Example 15

The device of any one or more of Example 1 through Example 14, wherein the actuator is configured to provide pre-tension to the stabilization assembly.

Example 16

The device of any one or more of Example 1 through Example 15, wherein the device comprises two or more stabilization assemblies.

Example 17

The device of any one or more of Example 4 through Example 10 and Example 12 through Example 16, wherein the frame assembly comprises a U-shape.

Example 18

The device of any one or more of Example 1 through Example 17, wherein the stabilization assembly defines a proximal end and a distal end, wherein the distal end is configured to receive the stabilization feature, the stabilization assembly further defines an axis extending from the proximal end to the distal end, wherein the actuator positioned at the second location is located along a different axis from the axis defined by the stabilization assembly.

Example 19

An apparatus configured for use with a patient stabilization device, wherein the apparatus regulates an amount of force applied to the patient by the stabilization device, the apparatus comprising: (a) a first body having a first end and a second end, wherein the first end is configured to connect with a stabilization assembly of the stabilization device; and (b) an actuator, directly or indirectly connectable with the first body, wherein the actuator is configured to cause a torque to be applied on the first body, wherein an increase in the torque on the first body increases a tension within the first body, wherein the first body applies an increase in force to the stabilization assembly in response to the increase in tension within the first body.

Example 20

The device of Example 19, wherein the first body is rigid.

Example 21

The device of any one or more of Example 19 through Example 20, wherein the dimensions of the first body remain constant when the torque is applied on the first body and when the tension increases within the first body.

Example 22

The device of any one or more of Example 19 through Example 21, further comprising a second body connecting with the first body at the second end in a keyed manner such that the first body and the second body are prevented from rotating relative to one another.

Example 23

The device of Example 22, wherein the second body and the first body are oriented substantially perpendicular to one another.

Example 24

The device of any one or more of Example 22 through Example 23, wherein the second body is rigid.

Example 25

The device of any one or more of Example 22 through Example 24, wherein the actuator is directly or indirectly connectable with the second body, wherein the actuator is configured to cause the torque to be applied on the first body by causing the torque to be applied on the second body and transferred to the first body such that the tension within the first body increases.

Example 26

The device of any one or more of Example 22 through Example 25, wherein the dimensions of the second body remain constant when the torque is applied on the second body causing the increase in tension within the first body.

Example 27

A device for stabilizing a patient comprising: (a) a frame having a receiving portion and a pin extending transversely through the receiving portion; and (b) a stabilization assembly having a stabilization feature configured to contact the patient, the stabilization assembly configured for selective receipt within the receiving portion, the stabilization assembly having a housing comprising: (i) a slot located in a proximal side of the housing, wherein the slot is configured to receive the pin extending transversely through the receiving portion of the frame, and (ii) a first retention feature movable relative to the housing from a first position to a second position, wherein in the first position the first retention feature allows the pin of the frame to fully seat within the slot of the housing such that the stabilization assembly is fully seated within the receiving portion of the frame, wherein in the second position the first retention feature secures the stabilization assembly within the receiving portion.

Example 28

The device of Example 27, wherein the housing comprises a bore located in a distal side of the housing, wherein the bore is configured to selectively retain the stabilization feature.

Example 29

The device of any one or more of Example 27 through Example 28, wherein the housing comprises a first resilient feature connectable with the first retention feature, wherein the first resilient feature has a bias that maintains the first retention feature in the second position within the housing, wherein the first retention feature is movable to the first position by compressing the first resilient feature.

Example 30

The device of any one or more of Example 27 through Example 29, comprising an adjustment feature configured to set a width of the frame.

Example 31

The device of any one or more of Example 27 and Example 29 through Example 25, wherein the housing comprises a bore located in a distal side of the housing, wherein the device further comprises an adapter selectively retained within the bore of the housing, wherein the adapter is configured to selectively retain the stabilization feature.

Example 32

The device of Example 31, wherein the adapter comprises an engagement feature.

Example 33

The device of any one or more of Example 31 through Example 32, the housing comprises a second retention feature movable relative to the housing, wherein the second retention feature is configurable to align and engage with the engagement feature of the adapter, wherein engagement between the second retention feature and the engagement feature of the adapter secures the adapter within the bore of the housing.

Example 34

The device of any one or more of Example 31 through Example 33, wherein securing the adapter within the bore of the housing prevents translational movement of the adapter within the bore of the housing yet permits rotational movement of the adapter relative to the housing.

Example 35

The device of any one or more of Example 32 through Example 34, wherein the engagement feature of the adapter comprises an annular groove and the second retention feature comprises a rounded member configured to fit within the annular groove.

Example 36

The device of any one or more of Example 33 through Example 35, wherein the housing comprises a second resilient feature connectable with the second retention feature, wherein the second resilient feature has a bias that maintains the second retention feature in an extended position within the housing that maintains engagement of the second retention feature with the engagement feature of the adapter, wherein the second retention feature is movable to disengage from the engagement feature of the adapter by compressing the second resilient feature.

Example 37

A device for stabilizing a head of a patient, the device comprising: (a) a frame comprising a receiving portion; and (b) a stabilization assembly configured for receipt within the receiving portion, wherein the stabilization assembly is configured to retain one or more stabilizing features configured to contact the head of the patient, wherein the stabilization assembly comprises: (i) a selectively rotatable member, (ii) an actuator configured to translate longitudinally to move the actuator between a first position and a second position, wherein in the first position the selectively rotatable member is rotationally adjustable, and wherein in the second position the selectively rotatable member is rotationally fixed, wherein the actuator comprises a locking member having a first engaging feature, and (iii) a holder connectable with the selectively rotatable member, wherein the holder comprises a second engaging feature configured for selective engagement with the first engaging feature, wherein the first and second engaging features are longitudinally translatable relative to one another to selectively engage and disengage the first and second engaging features and thereby adjust or fix a rotational position of the rotatable member.

Example 38

The device of Example 37, the actuator comprising a depressible member configured to move between a third position and a fourth position, wherein the depressible member is biased to the third position, and wherein to move the actuator between the first and second positions, the depressible member is moved from the third position to the fourth position to overcome the bias.

Example 39

The device of any one or more of Example 37 through Example 38, the locking member with the first engaging feature is advanced longitudinally away from the rotatable member when the actuator is moved from the first position to the second position.

Example 40

The device of any one or more of Example 37 through Example 38, the locking member with the first engaging feature is advanced longitudinally toward the rotatable member when the actuator is moved from the first position to the second position.

Example 41

The device of any one or more of Example 37 through Example 40, the first engaging feature and second engaging feature each comprising a toothed ring configuration.

Example 42

The device of any one or more of Example 38 through Example 41, the rotatable member being maintainable in either a rotatably adjustable state or a fixed state with the actuator in the third position.

Example 43

The device of Example 37, the actuator comprising a depressible member and an inset member, the depressible member selectively engageable with the inset member, wherein engagement between the depressible member and inset member maintains the rotatable member in a select one of a rotatably adjustable state or a fixed state depending on a longitudinal position of the actuator.

Example 44

The device of any one or more of Example 37 through Example 43, wherein a user is permitted to set up the stabilization assembly to a desired rotational position without the user maintaining contact with the actuator while making rotational adjustments.

Example 45

The device of Example 37, the depressible member is biased to a third position and configured to move between the third position and a fourth position, wherein in the third position the depressible member engages with the inset member, and in the fourth position the depressible member disengages from the inset member.

Example 46

A stabilization assembly for use with a patient stabilizing device, wherein the stabilization assembly comprises: (a) a selectively rotatable member configured to retain one or more stabilization features configured to contact the patient; and (b) a pair of engaging features configured to longitudinally translate relative to one another from a first position to a second position, wherein in the first position the pair of engaging features are engaged and the selectively rotatable member is fixed, and wherein in the second position the pair of engaging features are disengaged and the selectively rotatable member is rotationally adjustable.

Example 47

A device for stabilizing a patient comprising: (a) a frame having a first receiving portion; (b) a first stabilization assembly configured to receive one or more stabilization features, wherein the first stabilization assembly is further configured to connect with the first receiving portion of the frame, wherein the first stabilization assembly comprises: (i) a housing, wherein the housing connects with the first receiving portion of the frame, (ii) an arm connectable with the housing and configured to receive the one or more stabilization features, wherein the arm is configured to adopt a first state in which the arm is rotatable relative to the housing, and wherein the arm is configured to further adopt a second state in which the arm is not rotatable relative to the housing, (iii) a first actuator configured to place the arm in the second state, and (iv) a second actuator configured to place the arm in the first state.

Example 48

The device of Example 47, wherein the first actuator is connectable with the housing and comprises a first engaging feature configured to contact a second engaging feature associated with the arm to fix the rotational position of the arm.

Example 49

The device of Example 48, wherein the second actuator is connectable with the housing and biased to maintain the first engaging feature of the first actuator in contact with the second engaging feature, wherein overcoming the bias of the second actuator permits disengagement of the first engaging feature from the second engaging feature to permit rotational adjustment of the arm.

Example 50

The device of any one or more of Example 48 through Example 49, wherein the first actuator is biased to disengage a first engaging feature from a second engaging feature associated with the arm.

Example 51

The device of Example 50, wherein overcoming the bias of the first actuator causes the first engaging feature to engage or contact the second engaging feature, and further to permit a bias of the second actuator to maintain this engagement between the first and second engaging features.

Example 52

The device of any one or more of Example 47 through Example 51, wherein the frame further comprises a second receiving portion, and wherein the device comprises a second stabilization assembly connectable with the second receiving portion.

Example 53

A device for stabilizing a patient comprising: (a) a frame having a first member and a second member, wherein the position of the first and the second members is adjustable to change a relative position of the first and the second members with respect to one another; (b) an actuator connectable with the frame; and (c) a first locking feature connectable with the actuator, wherein the actuator is configured to move the first locking feature between a first position and a second position, wherein in the first position the first locking feature provides for a friction fit that prevents movement of the first and the second members of the frame away from one another, wherein in the second position the first locking feature permits movement of the first and the second members of the frame away from one another.

Example 54

The device of Example 53, the device comprising a skull clamp for stabilizing a head of the patient.

Example 55

The device of any one or more of Example 53 through Example 54, comprising a second locking feature configured to contact the first locking feature.

Example 56

The device of Example 55, wherein the second locking feature and a portion of the first locking feature each comprise a sloped surface, wherein each of the sloped surfaces is configured for contacting the other.

Example 57

The device of any one or more of Example 55 through Example 56, wherein translation of the first locking feature in a first direction causes the first locking feature to drive the second locking feature into contact with a portion of the frame.

Example 58

A device for stabilizing a patient comprising: (a) a frame having a first member and a second member, wherein the position of the first and the second members is adjustable to change a relative position of the first and the second members with respect to one another; (b) an actuator connectable with the frame; and (c) a first locking feature connectable with the actuator, wherein the actuator is configured to move the first locking feature between a first position and a second position, wherein in the first position the first locking feature provides for a stepless fit that prevents movement of the first and the second members of the frame away from one another, wherein in the second position the first locking feature permits movement of the first and the second members of the frame away from one another, and wherein the stepless fit provides for infinitely variable adjustment increments for spacing the first and second members relative to each other.

Example 59

The device of Example 58, the device comprising a skull clamp for stabilizing a head of the patient.

Example 60

The device of any one or more of Example 58 through Example 59, comprising a second locking feature configured to contact the first locking feature.

Example 61

The device of Example 60, wherein the second locking feature and a portion of the first locking feature each comprise a sloped surface, wherein each of the sloped surfaces is configured for contacting the other.

Example 62

The device of any one or more of Example 60 through Example 61, wherein translation of the first locking feature in a first direction causes the first locking feature to drive the second locking feature into contact with a portion of the frame.

VIII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for stabilizing a patient comprising:
   (a) a frame assembly having a first frame portion that defines a lateral portion and an upright portion, wherein the upright portion includes a receiving portion, wherein the upright portion that includes the receiving portion defines a first location;
   (b) a stabilization assembly configured to be received by the receiving portion of the upright portion of the first frame portion at the first location, the stabilization assembly defines a proximal end and a distal end and an axis that extends from the proximal end to the distal end;
   (c) a stabilization feature configured to be received by the stabilization assembly, the stabilization feature configured to contact the patient; and
   (d) a tensioning feature configured to connect with the stabilization assembly at the first location, the tensioning feature includes an actuator positioned at a second location spaced a distance away from the first location such that the actuator is spaced away from the stabilization assembly and along a different axis from the axis defined by the stabilization assembly, the tensioning feature includes an elongated member extending from the actuator along the upright portion of the first frame portion to the stabilization assembly, the tensioning feature includes a body at the second location with the actuator where the actuator is configured to move the elongated member relative to the body to transfer a force to the elongated member to transfer at least a portion of the force to the stabilization assembly to increase an amount of force the stabilization assembly is configured to impart onto the patient.

2. The device of claim 1, further comprising a second frame portion, the first and second frame portions are selectively movable relative to one another to adjust a space between the first and second frame portions.

3. The device of claim 2, the tensioning feature being configured to adjust the amount of force the stabilization assembly is configured to impart onto the patient while maintaining a relative position of the first and second frame portions such that the space between the first and second frame portions is unchanged.

4. The device of claim 2, the tensioning feature being configured to adjust the amount of force the stabilization assembly is configured to impart onto the patient while a relative position of the first and second frame portions changes as the amount of force the stabilization assembly is configured to impart onto the patient is adjusted such that the space between the first and second frame portions is changed.

5. The device of claim 1, further comprising a force indication feature configured to indicate the amount of force the stabilization assembly is configured to impart onto the patient.

6. The device of claim 5, the force indication feature including a plurality of indicators, wherein the elongated member is movable relative to the plurality of indicators to indicate the amount of force the stabilization assembly is configured to impart onto the patient.

7. The device of claim 1, at least a portion of the elongated member being configured to bend in response to an increase in force imparted to the stabilization assembly.

8. The device of claim 1, the actuator configured to transmit rotary motion to the body, the body having a cylindrical portion including threading, the threading being configured to engage threading of the elongated member to move the elongated member relative to the body.

9. The device of claim 1, further comprising a second frame portion, the actuator configured to transmit rotary motion to the body, the body having a cylindrical portion including threading, the threading being configured to engage threading of the second frame portion to move the second frame portion and the elongated member relative to the first frame portion.

10. The device of claim 1, the actuator further comprising a rod and a lock feature configured to releasably hold the rod in a selected position of a plurality of predetermined positions relative to the body.

11. The device of claim 1, further comprising a second frame portion, and an adjustment feature configured to adjust a relative position of the first and second frame portions to overcome the force applied to the stabilization assembly by the tensioning feature.

12. The device of claim 1, wherein the tensioning feature comprises a torsion rod, wherein a torque on the torsion rod transfers the force to the elongated member, and wherein the elongated member transfers at least the portion of the force to the stabilization assembly to increase the amount of force the stabilization assembly is configured to impart onto the patient.

13. The device of claim 1, wherein the tensioning feature is configured to apply the amount of force to the stabilization assembly via a twisting action.

14. The device of claim 1, wherein the actuator is configured to provide pre-tension to the stabilization assembly.

15. The device of claim 1, wherein the distal end of the stabilization assembly is configured to receive the stabilization feature.

* * * * *